US011931196B1

United States Patent
Kingma et al.

(10) Patent No.: US 11,931,196 B1
(45) Date of Patent: Mar. 19, 2024

(54) MEDICAL IMAGING SYSTEMS FOR REDUCING RADIATION EXPOSURE

(71) Applicant: RADuxtion, LLC, Fishers, IN (US)

(72) Inventors: Phillip R. Kingma, Fishers, IN (US); Letrisha Weber, Indianapolis, IN (US)

(73) Assignee: RADuxtion, LLC, Fishers, IN (US)

( * ) Notice: Subject to any disclaimer, the term of this patent is extended or adjusted under 35 U.S.C. 154(b) by 0 days.

(21) Appl. No.: 18/369,349

(22) Filed: Sep. 18, 2023

(51) Int. Cl.
*A61B 6/00* (2006.01)
*G06T 7/00* (2017.01)
*G16H 40/20* (2018.01)
*G16H 40/40* (2018.01)
(Continued)

(52) U.S. Cl.
CPC .............. *A61B 6/544* (2013.01); *A61B 6/545* (2013.01); *G06T 7/0012* (2013.01); *G16H 40/20* (2018.01); *G16H 40/40* (2018.01); *G16H 40/67* (2018.01); *G06T 2200/24* (2013.01); *G06T 2207/10121* (2013.01); *G06T 2207/20081* (2013.01); *G06T 2207/20084* (2013.01); *G06T 2207/30168* (2013.01); *G16H 10/60* (2018.01)

(58) Field of Classification Search
CPC ....... A61B 6/544; A61B 6/545; G06T 7/0012; G06T 2200/24; G06T 2207/10121; G06T 2207/20081; G06T 2207/20084; G06T 2207/30168; G16H 40/20; G16H 40/40; G16H 40/67; G16H 10/60
See application file for complete search history.

(56) References Cited

U.S. PATENT DOCUMENTS

| 5,293,415 A | 3/1994 | Hartley et al. |
| 7,490,987 B2 | 2/2009 | Busch |
| 7,620,142 B1 | 11/2009 | Toth |
| (Continued) | | |

FOREIGN PATENT DOCUMENTS

| EP | 3367900 A1 | 9/2018 |
| EP | 2491506 B1 | 12/2019 |
| JP | 2009042247 A | 2/2009 |

OTHER PUBLICATIONS

Oct. 5, 2023—(WO) Written Opinion of the International Searching Authority—App PCT/US2022/012862.
(Continued)

*Primary Examiner* — Courtney D Thomas
(74) *Attorney, Agent, or Firm* — Banner & Witcoff, Ltd.

(57) ABSTRACT

Methods, systems, and apparatuses are described herein for using processes and machine learning techniques to optimize medical imaging processes to reduce inadvertent exposure to harmful radiation. A machine learning model may be trained to output recommended medical imaging device operating parameter settings. Available operating parameters of a medical imaging device may be determined, and patient data may be received. The patient data and the available operating parameters may be used as input to the trained machine learning model, which might output recommended operating parameter settings. In turn, this output in addition to other calculations might be used to transmit, to the medical imaging device, data that causes modification of the operating parameters of the medical imaging device. Metadata corresponding to one or more images captured by the medical imaging device may be received, and the trained machine learning model might be further trained based on that metadata.

14 Claims, 13 Drawing Sheets

(51) Int. Cl.
*G16H 40/67* (2018.01)
*G16H 10/60* (2018.01)

(56) References Cited

U.S. PATENT DOCUMENTS

| | | | |
|---|---|---|---|
| 7,949,098 | B2 | 5/2011 | Ellinwood et al. |
| 8,903,037 | B2 | 12/2014 | Yu et al. |
| 9,275,189 | B2 | 3/2016 | Walker et al. |
| 9,323,896 | B2 | 4/2016 | Fält et al. |
| 9,592,022 | B2 | 3/2017 | Larson |
| 10,085,698 | B2 | 10/2018 | Fan et al. |
| 2004/0131141 | A1 | 7/2004 | Horiuchi |
| 2005/0031080 | A1* | 2/2005 | Klingenbeck-Regn ............... A61B 5/1072 378/95 |
| 2007/0076842 | A1 | 4/2007 | Tkaczyk et al. |
| 2010/0091950 | A1 | 4/2010 | Ellinwood et al. |
| 2019/0099148 | A1 | 4/2019 | Rupcich et al. |
| 2019/0108905 | A1 | 4/2019 | Zhang et al. |
| 2021/0137482 | A1 | 5/2021 | Bernhardt et al. |
| 2021/0267564 | A1 | 9/2021 | Brody |
| 2022/0240883 | A1 | 8/2022 | Kingma et al. |

OTHER PUBLICATIONS

Hernanz-Schulman et al., Pause and Pulse: ten Steps That Help Manage Radiation Dose during Pediatric Fluoroscopy, Pediatric Imaging.Review, Aug. 2011 pp. 475-481.
Mahesh, Imaging & Therapeutic Technology, Fluoroscopy: Patient Radiation Exposure Issues, Radiographies, Jul. 2001, vol. 21, Issue 4.
Agnew, C., et al. (2021). Optimisation of Varian TrueBeam head, thorax and pelvis CBCT based on patient size. Journal of Radiotherapy in Practice, 20(3), 248-256. doi: 10.1017/S1460396920000618.
Ketelsen et al., Automated Corrupted Tomography Dose-Saving Algorithm to Protect Radiosensitive Tissues Estimation of Radiation Exposure and Image Quality Considerations; Investigative Radiology 47(2)p. 148-152 Feb. 2012.
Yu et al., Automatic selection of tube potential for radiation dose reduction in CT: a general strategy; Jan. 2010 Med Phys. 37(1): 234-43.

* cited by examiner

MEDICAL IMAGING SYSTEMS FOR REDUCING RADIATION EXPOSURE

FIELD OF USE

Aspects of the disclosure relate generally to medical imaging systems, such as fluoroscopy devices and x-ray devices. More specifically, aspects of the disclosure may provide for reducing or eliminating high doses of harmful radiation by using a combination of patient-specific data and/or machine learning techniques.

BACKGROUND

Medical imaging devices, such as fluoroscopy imaging devices and x-ray imaging devices, may be used to create a visual representation of the internal structures of the human body, animals or other inanimate objects. While these imaging devices are very useful, they can emit harmful radiation to both the subject being imaged or scanned and nearby objects (e.g., radiology technologists, doctors, and the like). For instance, a typical medical imaging system may extend exposure to 0.5 secs or more, with radiation detectable to 6 feet and beyond at a scatter rate of over 300 millirems per hour (mRem/hour) or more for every image generated during a given imaging session. Excessive exposure to such radiation can cause a variety of ailments, such as cataracts and various forms of cancer.

Misconfiguration and/or misuse of medical imaging devices can increase the incidence of radiation exposure to the subject being scanned and nearby objects. For example, some radiology technologists iteratively use medical imaging devices in manual mode until a desired image is received—that is, the radiology technologist might take capture a first image using a medical imaging system, evaluate the quality of the image, modify operating parameters (e.g., kVp, mAs) of the medical imaging system, and then re-take the image. Most commonly, this process (iteratively imaging, evaluating image quality, modifying parameters, and re-imaging) is automated in a process known as Automated Exposure Control (AEC). AEC is a safety feature commonly used on more modern imaging devices to reduce radiation exposure. That said, every new image exposes the subject and nearby objects to further radiation. While that might not be a significant problem for a patient that is only scanned a few times in their life, this might pose a significant risk for nearby doctors and radiology technologists, who might be exposed to such radiation on a regular basis.

SUMMARY

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below.

Aspects described herein relate to using machine learning to improve the process by which medical imaging systems are configured such that the overall exposure to patients, clinical personnel, and the like is reduced. To achieve this goal, aspects described herein relate to training a machine learning model based on medical imaging device operating parameter settings, patient data, and imaging results, developing a fulsome model of idealized parameter settings that takes into account variables such as patient height/weight, eccentricates of particular medical imaging system models, and the operating parameters available on different models of medical imaging systems. This trained machine learning model might then be provided information about available operating parameters for a particular medical imaging system and patient data, and the trained machine learning model may then output recommended operating parameter settings. These recommended operating parameter settings might be used, along with other considerations, to create instructions for the medical imaging system. Metadata about image(s) captured by the medical imaging system might then be used to further train the model, ensuring that the model iteratively learns over time. This process has numerous benefits revealed during testing. On one hand, the medical imaging system performs more accurately, more quickly, reducing the total radiation exposure to both subject and those around the subject, such as doctors and staff. On the other hand, this process also lowers the overall power consumption and radiation output of medical imaging systems overall, which saves significant money, improves the longevity of the systems, and also lessens the chance that medical imaging systems become temporarily unavailable due to overheating issues.

More particularly, a computing device may generate a trained machine learning model by training, using training data comprising a history of medical imaging device operating parameter settings, patient data, and imaging results, a machine learning model to output recommended medical imaging device operating parameter settings. Training the machine learning model may comprise modifying, based on the training data, one or more weights of one or more nodes of an artificial neural network. The computing device may receive an indication of a medical imaging device and determine, based on the indication of the medical imaging device, available operating parameters of the medical imaging device. The computing device may then receive patient data. This patient data might be received via a user interface: for example, the computing device may cause display, via a user device, of a user interface and receive, via the user interface, a patient weight and a patient height. In addition, the patient data may be captured using an image capture device (e.g., a digital camera) that then translates the image into patient specific data such as patient height, weight, volume, mass, etc. The computing device may then provide, to one or more input nodes of the trained machine learning model, the patient data and data corresponding to the available operating parameters of the medical imaging device. In response, the computing device may receive, via one or more output nodes of the trained machine learning model, one or more recommended operating parameter settings. The computing device may then transmit, to the medical imaging device, data that causes modification of operating parameters of the medical imaging device based on the one or more recommended operating parameter settings. For example, the data may be configured to cause the medical imaging device to set an auto feature off and capture a quantity of images at a predetermined interval or rate. Metadata corresponding to one or more images captured by the medical imaging device may be received, and the computing device may further train, based on the metadata, the trained machine learning model. That metadata might relate to any aspect of the one or more images: for example, the computing device may determine the metadata by processing the one or more images to identify an image quality for each of the one or more images.

The trained machine learning model might be continually improved based on a variety of information about medical imaging systems. This may include instances where the computing device causes modification of the operating parameters of the medical imaging device, but a technologist makes even further modifications to those parameters (e.g., indicating that further changes had to be made). For example, the computing device may determine one or more further modifications made to the operating parameters of the medical imaging device, and further training the trained machine learning model may be based on the one or more further modifications.

The computing device may modify operating parameters of the medical imaging system in a variety of ways, and the data sent to the medical imaging system need not exclusively be based on the output of the trained machine learning model. For example, the computing device may determine the data based on the patient data, the one or more recommended operating parameter settings, or the like.

The computing device may determine what operating parameters it can control based on database-stored information about a variety of different medical imaging systems. For example, as part of determining the available operating parameters of a medical imaging device, the computing device may query, based on the indication of the medical imaging device, a database of device identifications and corresponding operating parameters.

The metadata corresponding to the one or more images captured by the medical imaging device may comprise any information about the one or more images. For instance, as part of receiving the metadata, the computing device may determine a quantity of the one or more images captured by the medical imaging device, whether a pulse setting was activated during capture of the one or more images, and/or whether an auto setting was activated during capture of the one or more images.

Corresponding methods, apparatus, systems, and non-transitory computer-readable media are also within the scope of the disclosure.

These features, along with many others, are discussed in greater detail below.

BRIEF DESCRIPTION OF THE DRAWINGS

The present disclosure is illustrated by way of example and not limited in the accompanying figures in which like reference numerals indicate similar elements and in which.

DETAILED DESCRIPTION

Figure 1:
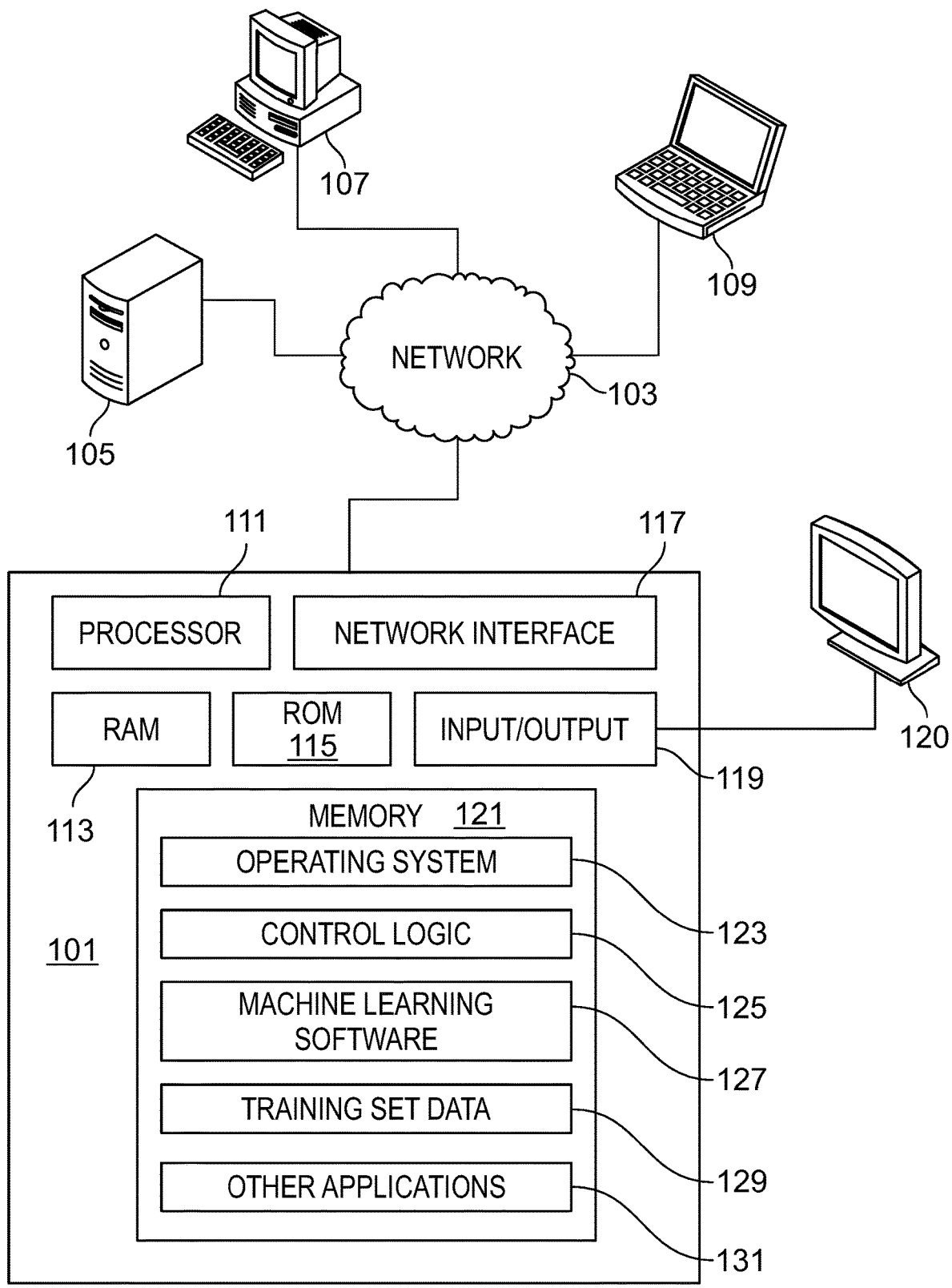
FIG. 1 depicts an example of a computing device that may be used in implementing one or more aspects of the disclosure in accordance with one or more illustrative aspects discussed herein.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof.

By way of introduction, misconfiguration of medical imaging devices can cause significant harm to patients and those around medical imaging devices. For example, many medical imaging devices use an AEC to capture images, evaluate those images, modify operating parameters, and re-take images, but this iterative process might be undesirable because every image capture might unnecessarily expose the patient and those nearby to significant quantities of radiation. Moreover, using AEC can require significant amounts of power and can increase the heat of components of the medical imaging system, which in some cases can cause the medical imaging system to overheat. Aspects described herein address those and other problems by using machine learning techniques, databases, and algorithms reliant on patient information to optimally configure a wide variety of medical imaging devices, lowering the number of images that need be captured and thereby lowering radiation exposure while also lowering power consumption and lowering the possibility that such medical imaging devices need to shut down due to heat concerns. Moreover, aspects described herein continually train such machine learning models, using image quality data to further train and thereby improve the accuracy of such models and thus further improving the ability of the medical imaging devices to capture desirable images without additional exposure to radiation.

As an example of how the present disclosure may operate, a radiology technologist may desire to use a fluoroscopy device to image the shoulder of a patient. The technologist may log into a user interface of a user device (e.g., a laptop) and provide, via the user interface, an indication of the medical imaging device (e.g., a name of the device, a nickname for the device, a manufacturer of the device, a model type of the device, or the like). The technologist may provide further information, such as an imaging specialty type, patient data such as patient height, weight, sex, age, whether the patient has osteoporosis or implants, or the like, information about the area to be imaged (e.g., the patient's left shoulder), and/or other relevant information. The computing device may then determine available operating parameters for the fluoroscopy device based on the data provided by the technologist. Based on those available operating parameters, the computing device might determine preliminary operating parameters using an algorithm. Additionally, the computing device might provide, to a trained machine learning model, all or portions of the data referenced above, and the trained machine learning model might output recommended operating parameters. The preliminary operating parameters and recommended operating parameters might be compared (e.g., averaged) and instructions based on either/both sets of parameters might be sent to the fluoroscopy device. Then, the quality of images captured by the fluoroscopy device might be used to further train the machine learning model. For example, if the images were of good quality, then the corresponding operating parameters might be provided to the trained machine learning model as an example of a good setting for that particular type of patient when scanning their shoulder.

Aspects described herein act as an improvement to medical imaging devices, including, but not limited, x-ray devices and fluoroscopy devices (both mobile and stationary devices). As detailed above, misuse and/or misconfiguration of medical imaging devices can be dangerous (e.g., can expose others to additional radiation), can lower the operating life of medical imaging devices, can waste power, and can make medical imaging devices time-consuming and difficult to use (particularly when those devices have to temporarily shut down for overheating issues). The present disclosure uses machine learning techniques and other approaches to improve the starting settings for such medical imaging devices, meaning that they take better images faster.

Test results indicate that the present disclosure significantly reduces the exposure of the patient and third parties to excess radiation (e.g., depending on the study and patient conditions, more than a 68-79% dose reduction). As part of the process leading to the present disclosure, a study was conducted of four different imaging machines to compare standard settings (that is, manufacturer-recommended settings implemented via AEC) with settings derived based on the techniques described herein. As part of this process, various dosimeters were used to measure mRem of radiation at different distances from the imaging machine. As demonstrated by Table 1 below, the present disclosure involves operating parameters which significantly reduce radiation exposure at short distances from the imaging machines and all but eliminated exposure at further distances.

TABLE 1

| Dosimeter Location | $1^{st}$ Standard Machine (mRem) | $2^{nd}$ Standard Machine (mRem) | Present Disclosure-Improved Machine (mRem) |
|---|---|---|---|
| 1 foot from machine | 1359 | 233 | 63 |
| 2 feet from machine | 302 | 92 | 24 |
| 3 feet from machine | 101 | 43 | 13 |
| 4 feet from machine | 42 | 17 | 3 |
| 5 feet from machine | 22 | 10 | None |
| 6 feet from machine | 18 | 6 | None |

TABLE 1-continued

| Dosimeter Location | $1^{st}$ Standard Machine (mRem) | $2^{nd}$ Standard Machine (mRem) | Present Disclosure-Improved Machine (mRem) |
|---|---|---|---|
| 7 feet from machine | 10 | None | None |
| 8 feet from machine | 8 | None | None |
| Phantom (Patient) | 1259 | 1839 | 514 |
| 2 feet waist level (Doctor) | 332 | 159 | 36 |
| 4 Feet (Radiology Technologist) | 42 | 17 | 3 |
| Control | 0 | 0 | 0 |

In this study, the patient dose was calculated using the total/cumulative exposure for 150 different patients, with 20 images per case, the doctor dose was calculated at a location approximately two feet from the imaging machine, and the radiation technologist dose was calculated at a location approximately four feet from the imaging machine. That said, while these number are fairly illustrative one skilled in the art would recognize that the reality of radiation production, patient variability, tissue density, and a multitude of other factors can yield different results in different circumstances.

Test results also indicate that the present disclosure significantly lowers heat generation by medical imaging devices because it makes those devices more accurate. In the same study referenced above, the first standard device (without the benefit of the present disclosure) had heat warnings output at the $74^{th}$ and the $121^{st}$ cases of the 150 cases. In the same 150-patient study referenced above, which used the second standard machine, the device output a heat warning in 136 of 150 cases. This forced the technologist to shut down the device for cooling for approximately thirty minutes. When the second standard device was used with the benefit of the present disclosure, not a single test involved output of a heat warning. In other words, with the benefit of the present disclosure, the second device was able to complete 150 cases with no heat warning. Without being bound to any theory of operation, this suggests that the processes were not merely more efficient (particularly time-efficient), but that less power might have been used.

Before discussing these concepts in greater detail, however, several examples of a computing device that may be used in implementing and/or otherwise providing various aspects of the disclosure will first be discussed with respect to FIG. 1.

FIG. 1 illustrates one example of a computing device 101 that may be used to implement one or more illustrative aspects discussed herein. For example, computing device 101 may, in some embodiments, implement one or more aspects of the disclosure by reading and/or executing instructions and performing one or more actions based on the instructions. In some embodiments, computing device 101 may represent, be incorporated in, and/or include various devices such as a desktop computer, a computer server, a mobile device (e.g., a laptop computer, a tablet computer, a smart phone, any other types of mobile computing devices, and the like), and/or any other type of data processing device.

Computing device 101 may, in some embodiments, operate in a standalone environment. In others, computing device 101 may operate in a networked environment. As shown in FIG. 1, computing devices 101, 105, 107, and 109 may be interconnected via a network 103, such as the Internet. Other networks may also or alternatively be used, including private intranets, corporate networks, LANs, wireless networks, personal networks (PAN), and the like. Network 103 is for illustration purposes and may be replaced with fewer or additional computer networks. A local area network (LAN) may have one or more of any known LAN topologies and may use one or more of a variety of different protocols, such as Ethernet. Devices 101, 105, 107, 109 and other devices (not shown) may be connected to one or more of the networks via twisted pair wires, coaxial cable, fiber optics, radio waves or other communication media.

As seen in FIG. 1, computing device 101 may include a processor 111, RAM 113, ROM 115, network interface 117, input/output interfaces 119 (e.g., keyboard, mouse, display, printer, etc.), and memory 121. Processor 111 may include one or more computer processing units (CPUs), graphical processing units (GPUs), and/or other processing units such as a processor adapted to perform computations associated with machine learning. I/O 119 may include a variety of interface units and drives for reading, writing, displaying, and/or printing data or files. I/O 119 may be coupled with a display such as display 120. Memory 121 may store software for configuring computing device 101 into a special purpose computing device in order to perform one or more of the various functions discussed herein. Memory 121 may store operating system software 123 for controlling overall operation of computing device 101, control logic 125 for instructing computing device 101 to perform aspects discussed herein, machine learning software 127, training set data 129, and other applications 131. Control logic 125 may be incorporated in and may be a part of machine learning software 127. In other embodiments, computing device 101 may include two or more of any and/or all of these components (e.g., two or more processors, two or more memories, etc.) and/or other components and/or subsystems not illustrated here.

Devices 105, 107, 109 may have similar or different architecture as described with respect to computing device 101. Those of skill in the art will appreciate that the functionality of computing device 101 (or device 105, 107, 109) as described herein may be spread across multiple data processing devices, for example, to distribute processing load across multiple computers, to segregate transactions based on geographic location, user access level, quality of service (QoS), etc. For example, computing devices 101, 105, 107, 109, and others may operate in concert to provide parallel computing features in support of the operation of control logic 125 and/or machine learning software 127.

One or more aspects discussed herein may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects discussed herein, and such data structures are contemplated within the scope of computer executable instructions and computer-usable data described herein. Various aspects discussed herein may be embodied as a method, a computing device, a data processing system, or a computer program product.

Figure 2:
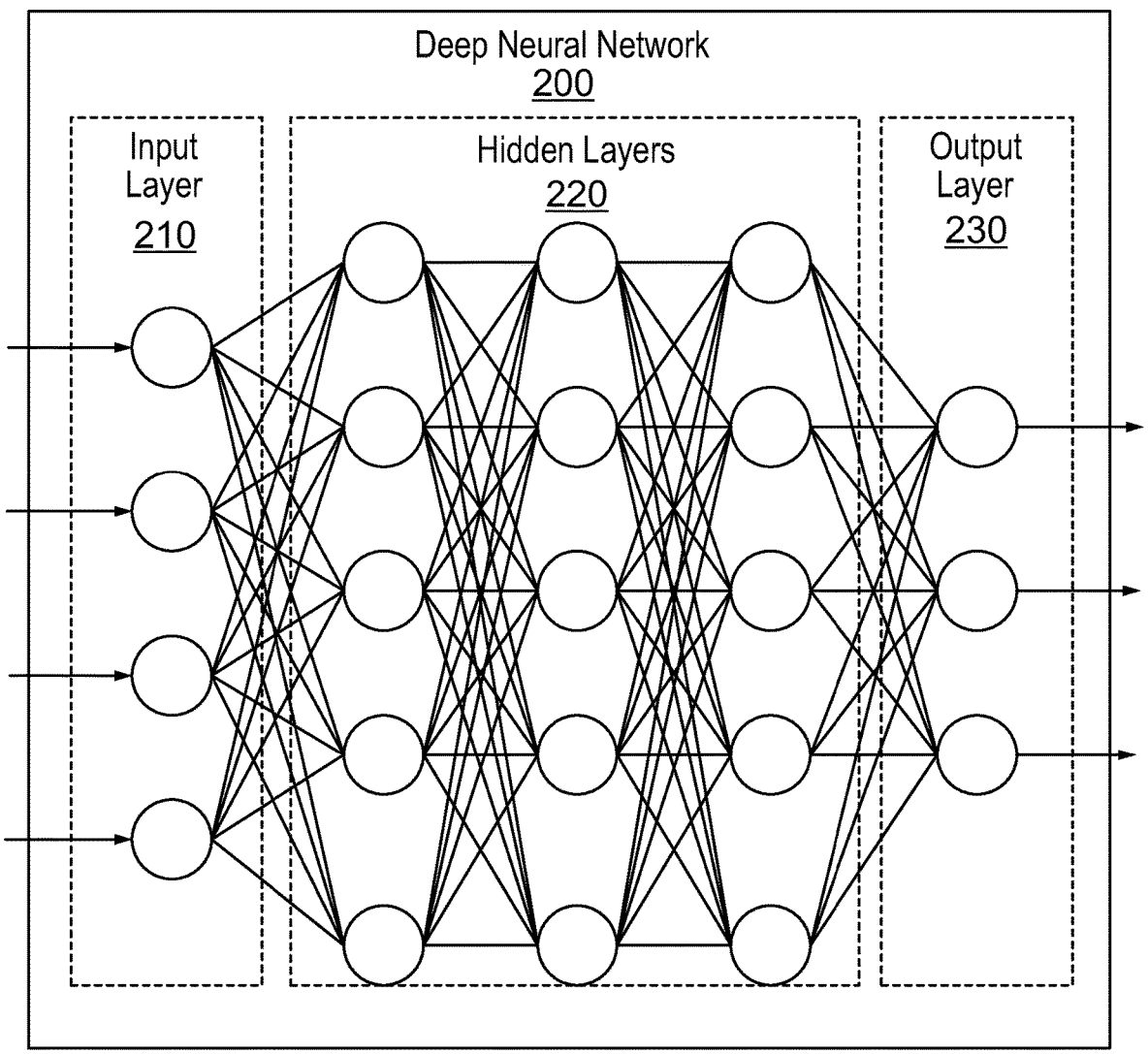
FIG. 2 depicts an example deep neural network architecture for a model according to one or more aspects of the disclosure.

FIG. 2 illustrates an example of a deep neural network architecture 200. Such a deep neural network architecture may be all or portions of the machine learning software 127 shown in FIG. 1. That said, the architecture depicted in FIG. 2 need not be performed on a single computing device, and may be performed by, e.g., a plurality of computers (e.g., one or more of the devices 101, 105, 107, 109). An artificial neural network may be a collection of connected nodes, with the nodes and connections each having assigned weights used to generate predictions. Each node in the artificial neural network may receive input and generate an output signal. The output of a node in the artificial neural network may be a function of its inputs and the weights associated with the edges. Ultimately, the trained model may be provided with input beyond the training set and used to generate predictions regarding the likely results. Artificial neural networks may have many applications, including object classification, image recognition, speech recognition, natural language processing, text recognition, regression analysis, behavior modeling, and others.

An artificial neural network may have an input layer 210, one or more hidden layers 220, and an output layer 230. A deep neural network, as used herein, may be an artificial network that has more than one hidden layer. Illustrated network architecture 200 is depicted with three hidden layers, and thus may be considered a deep neural network. The number of hidden layers employed in deep neural network architecture 200 may vary based on the particular application and/or problem domain. For example, a network model used for image recognition may have a different number of hidden layers than a network used for speech recognition. Similarly, the number of input and/or output nodes may vary based on the application. Many types of deep neural networks are used in practice, such as convolutional neural networks, recurrent neural networks, feed forward neural networks, combinations thereof, and others.

During the model training process, the weights of each connection and/or node may be adjusted in a learning process as the model adapts to generate more accurate predictions on a training set. The weights assigned to each connection and/or node may be referred to as the model parameters. The model may be initialized with a random or white noise set of initial model parameters. The model parameters may then be iteratively adjusted using, for example, stochastic gradient descent algorithms that seek to minimize errors in the model.

Figure 3:
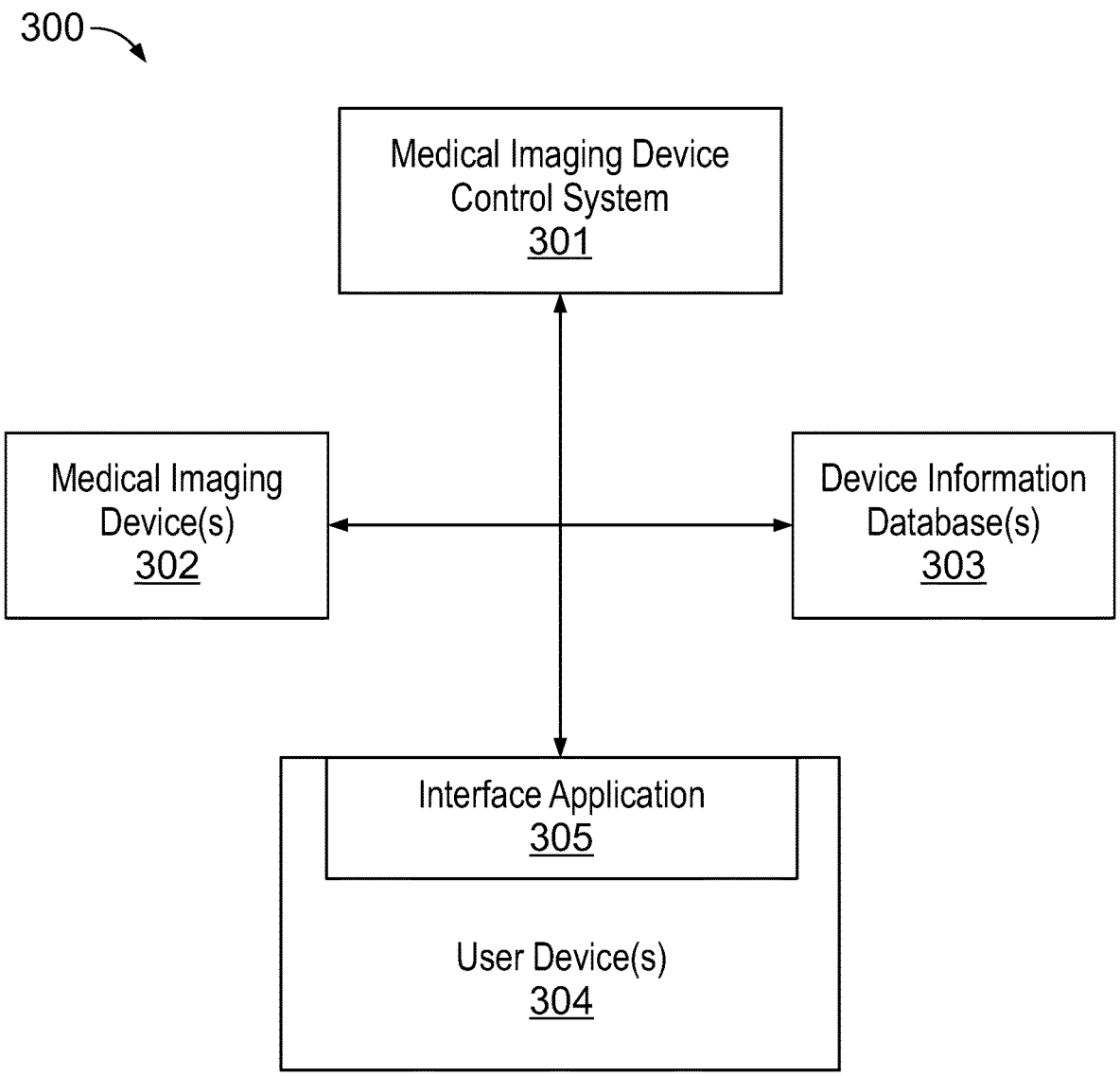
FIG. 3 depicts a system comprising servers and user devices.

FIG. 3 depicts a system 300 comprising a medical imaging device control system 301, one or more medical imaging devices 302, one or more device information databases 303, and one or more user devices 304 (which are shown executing an interface application 305). The medical imaging device control system 301, the one or more medical imaging devices 302, the one or more device information databases 303, and/or the one or more user devices 304 may comprise computing devices, such as computing devices that comprise one or more processors and memory storing instructions that, when executed on the one or more processors, cause the performance of one or more steps. The medical imaging device control system 301, the one or more medical imaging devices 302, the one or more device information databases 303, and/or the one or more user devices 304 may comprise any of the devices depicted with respect to FIG. 1, such as one or more of the computing devices 101, 105, 107, and/or 109.

The medical imaging device control system 301 may be configured to perform steps to optimize medical imaging processes associated with the one or more medical imaging devices 302 for the purposes of, for example, reducing inadvertent exposure to harmful radiation and making the one or more medical imaging devices 302 more efficient (which has, among other things, power use and heat generation benefits). The medical imaging device control system 301 may be configured to generate trained machine learning models using training data and using, for example, the neural network architecture 200 of FIG. 2. The medical imaging device control system 301 may be configured to receive data from the one or more user devices 304, such as patient data. The medical imaging device control system 301 may be configured to receive data from the one or more device information databases 303, such as information about the one or more medical imaging devices 302 (e.g., available operating parameters of those devices). The medical imaging device control system 301 may be configured to provide all or portions of that data to a trained machine learning model, and may be configured to receive output from that trained machine learning model. Using that output from the trained machine learning model, and based on other factors (e.g., other algorithms, models), the medical imaging device control system 301 may generate data that causes modification of operating parameters of the one or more medical imaging devices 302 and transmit such data to those devices. The medical imaging device control system 301 may receive metadata (e.g., quality information) relating to one or more images captured by the one or more medical imaging devices 302 and, using that metadata, further train the trained machine learning model. The metadata may be stored in a database (as described more below) and used either in real-time or at a later date.

The one or more medical imaging devices 302 may comprise any device which may perform imaging, such as a camera, a fluoroscopy machine, an x-ray machine, a computed tomography device, a magnetic resonance imaging device, or the like. Though termed a medical imaging device herein, the one or more medical imaging devices 302 need not be used for the purposes of medical diagnosis or similar goals. For example, the aspects described herein may be used for the purposes of improving the performance of a fluoroscopy machine used to image computer circuit boards. The one or more medical imaging devices 302 may have available operating parameters, which may comprise parameters which may be controlled (e.g., tuned) for the purposes of imaging. Such settings might include the duration of exposure, refresh rate, frame rate, resolution settings, post-processing settings, or the like. As such, the available operating parameters might be modified to improve images captured by the one or more medical imaging devices 302. The one or more medical imaging devices 302 may be configured to receive data which causes modification of those operating parameters. For example, the one or more medical imaging devices 302 may receive (e.g., via a network, via a Universal Serial Bus port, or the like) commands which cause the one or more medical imaging devices 302 to modify one or more operating parameters.

The one or more device information databases 303 may be configured to store information correlating medical imaging devices and operating parameters. For example, the one or more device information databases 303 may store a table that correlates medical device make and model with whether the corresponding medical device has an exposure setting. As another example, the one or more device information databases 303 may correlate unique device identifiers (e.g., serial numbers, device nicknames) with whether a particular device can operate in a pulsed photography mode. A high-level example of data that might be stored by the one or more device information databases 303 is provided below as Table 2.

TABLE 2

| Medical Imaging Device Identifier | Continuous Imaging? | Pulse Imaging? | Field of View Control? | Tube Age | Machine Hours |
|---|---|---|---|---|---|
| Office 2 | Y | N | Y | 1 year | 452 |
| S24AGNN2 | Y | N | N | 5 years | 3162 |
| Office 1 | N | Y | Y | 7 years | 4258 |
| Fluoroscopy Device 3 | N | Y | N | 10 years | 6524 |

In addition to the above, the one or more device information databases 303 may be configured to track variations across different medical imaging devices. Different medical imaging devices may have varying strength of radiation tubes, different tube ages, and the like. As such, even the same medical imaging device from the same manufacturer may behave differently and require different settings. In turn, the device information databases 303 may be configured to monitor medical imaging device variables and hours of service.

The one or more user devices 304 may comprise user devices (e.g., smartphones, laptops, desktop computers, tablets) that may execute the interface application 305 and may interface with the medical imaging device control system 301, the one or more medical imaging devices 302, and/or the one or more device information databases 303. For example, a user of the one or more user devices 304 may use the interface application 305 to send patient data to the medical imaging device control system 301, may use the interface application 305 to send an identifier of the one or more medical imaging devices 302 to the medical imaging device control system 301, and/or may use the interface application 305 to add, edit, and/or remove entries in the one or more device information databases 303.

Figure 4:
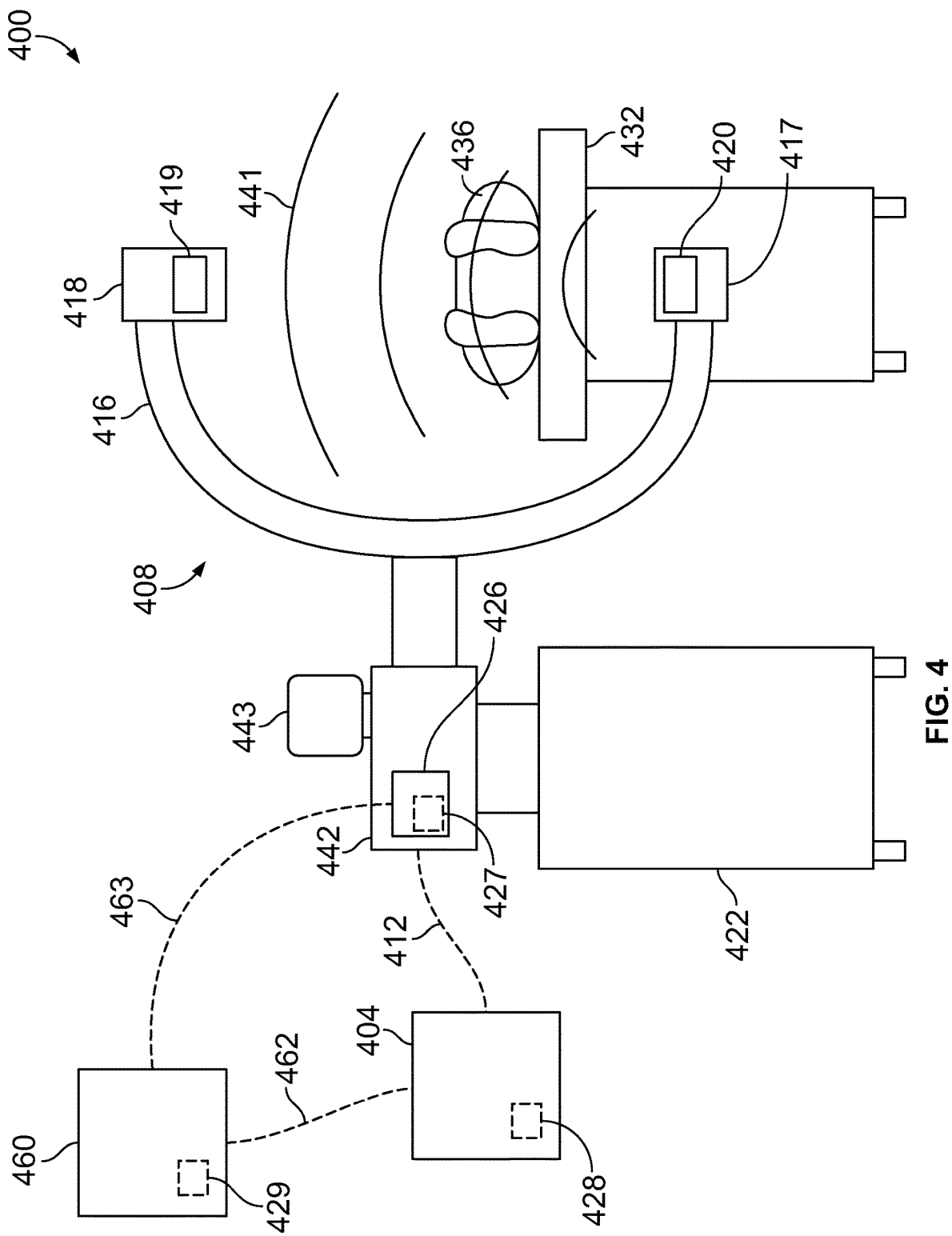
FIG. 4 depicts a medical imaging device.

FIG. 4 illustrates one example of components that may be included in a medical imaging device, such as the one or more medical imaging devices of FIG. 3. A medical imaging system 400 optionally includes a computer 404 (which may be the same or similar as the medical imaging device control system 301 and/or the one or more user devices 304) coupled to an imaging device 408 via an optional communication link 412. The communication link 412 may be of any suitable type, such as a wired connection between the computer 404 and the imaging device that uses coaxial cable, fiber optic cable, and the like. The communication link 412 may be a wireless connection using Wi-Fi, Bluetooth, LTE or any other suitable form of wireless communication. The computer 404 may collaborate with other computers such as a server 460 coupled to computer 404 by a communication link 462. The link 462 may also be any suitable wired or wireless connection that allow the computer 404 and the server 460 to determine one or more operational aspects or settings of the imaging system 400.

The imaging device 408 may include an imaging assembly 416, such as a C-arm, for capturing images of a subject 436. The subject 436 may be any suitable target for imaging, examples of which include, but are not limited to, a human or animal, a specimen, a patient in a hospital under the care of a doctor, or any object for which an image of the internal structure may be obtained using the imaging device. For instance, the subject 436 might comprise a video game controller to be scanned using an x-ray machine. The imaging device 408 may be any suitable type and may include one or more emitting or sensing elements. For example, the imaging assembly 416 may include a radiation source 417 useful for emitting electromagnetic energy 441 such as x-rays and an electromagnetic radiation detector 418 useful for detecting electromagnetic energy (preferably energy that has passed through the subject 436). The imaging assembly 416 is attached to a base 422, which may be mobile, and may include a controller 426 mounted within a housing 442. A user interface 443 may be part of the one or more user devices 304 and/or may be included in the imaging device which is configured to accept input from a user to provided operating parameters to the imaging device. These operating parameters may be provided to the controller 426, to the computer 404, to the server 460, and/or to other aspects of the imaging system to control the imaging process.

A support structure 432, such as a table, may be included to properly position subject 436 between the radiation source and radiation detector so that the electromagnetic energy 441 passing through may be used to generate an image of the internal structures of the subject. In this example, the radiation source 417 is oriented vertically below the subject, and the electromagnetic radiation detector 418 is above the subject; however, this configuration is only exemplary rather than restrictive as the source and detector aspects of the imaging assembly 416 may be arranged in any suitable configuration. For example, the source and detector may be inverted from what is shown with the detector below and the source above the subject, or they may be arranged horizontally with the subject standing, sitting, or otherwise positioned between the emitter and detector, to name a few other possible configurations.

The radiation source 417 may be any suitable type of emitter. In the case of an x-ray emitting radiation source, the radiation source 417 may include an x-ray tube configured to convert electrical input power into x-rays. The x-ray tube may include an evacuated chamber surrounding a heated filament often referred to as the cathode, the filament being positively charged and configured to generate a beam of electrons that strike an anode such as a rotating tungsten disk. The electrons may strike the anode at high-speed due to a very high potential difference between the cathode and the anode. The tungsten material absorbs the electrons and releases some of the energy in the form of x-rays.

Any suitable electromagnetic energy within the electromagnetic spectrum may be used by imaging device 408 to generate images, examples of which include but are not limited to, x-rays or gamma rays. For example, hard x-rays have a higher frequency than soft x-rays and may therefore be preferable for x-ray imaging because they generally penetrate a human or animal subject more easily thus making them more likely to pass through the subject and into the radiation detector. Soft x-rays may be used but may be less preferable for human or animal subjects because they are more likely to be absorbed in a subject's body, reducing the opportunity to generate a usable image while adding to the overall effective dose.

In one example, the imaging device 408 is configured to generate an internal image colloquially referred to as an "x-ray," "x-ray image," or more formally as a "radiograph." Such an internal image of a subject may be useful to assist with any imaging procedure such as medical procedures being performed in different regions of the subject's body. Examples of such procedures include, but are not limited to Computed Tomography (CT), an intravenous pyelogram, gastrointestinal x-rays, fluoroscopy, such as in the case of a catheter insertion or manipulation, placement of a stent in a blocked or partially blocked blood vessel, angiograms, or surgical procedures, to name a few non-limiting examples. In another example, the subject may be a manufactured article that is being imaged to detect abnormalities or defects using the disclosed system to generate an image of the internal structures of the item.

The internal image may be generated by directing electromagnetic energy 441 from the radiation source 417 toward the subject so that a portion of the radiation is absorbed by the body of the subject and a portion of the radiation is captured by the electromagnetic radiation detector 418, such as a fluoroscope or a digital x-ray detector such as a Flat Panel Detector (FDP). The imaging device 408 may include an image intensifier 419 that is operable to convert the captured radiation into visible light that has a higher intensity than what may be produced by the detector alone. This may allow a viewer to more easily see subtle aspects of the image than might otherwise be invisible. A collimator 420 may also be included for narrowing or focusing the x-ray radiation generated by the radiation source 417 to direct it more specifically on a particular region thus reducing the overall effective dose to the subject while increasing the likelihood of obtaining a clear image.

Different procedures may require the imaging device 408 to have different operating parameters in order to generate a useful image. In the case of x-rays, these operating parameters may include the voltage and the tube current exposure time product of the x-ray tube. The voltage may be measured by the kilovoltage peak (kVp), which describes the maximum voltage applied to the x-ray tube and is proportional to the energy of the x-ray photons emitted from the radiation source 417. Adjusting the kilovoltage peak may be used to adjust the contrast of the x-ray image, as different body parts may require a certain minimum kVp setting that will generate x-rays with enough energy to penetrate and pass through the target item or region of the body.

Another possible operational setting that may impact the image produced by imaging device 408 is the tube current exposure time product (mAs). The tube current exposure time is a calculation of the current passing through the x-ray tube creating the x-rays and the time that the tube is operated and may be used to control radiographic density. Larger values of the tube current exposure time product indicate greater radiation and can increase the number of x-ray photons that are absorbed by the body of the subject and that are collected by the electromagnetic radiation detector 418. As an example, a greater tube current exposure time product may be helpful when imaging larger areas of a subject, while a lower tube current exposure time may be sufficient for imaging smaller regions.

Controller 426 of the imaging device 408, which may be the same or similar as the medical imaging device control system 301 of FIG. 3, may be configured to control these and other operating parameters for the imaging assembly 416. For example, the controller 426 may activate (e.g., by transmitting appropriate data to the one or more medical imaging devices 302) an auto exposure mode that, among other aspects, automatically determines desirable operational settings by activating the imaging assembly 416 to generate multiple images in sequence using different combinations of kVp and mAs values for each image until an image of acceptable clarity is produced. That said, as discussed above, this repeated exposure to multiple imaging cycles results in additional radiation absorption by the subject, and by the individuals operating the imaging system. If this automated search for a desirable operational setting occurs multiple times in a given session, then the overall radiation absorption can be far in excess of the actual radiation required to generate one or two useful images thus increasing the overall radiation exposure per useful image.

Figure 5:
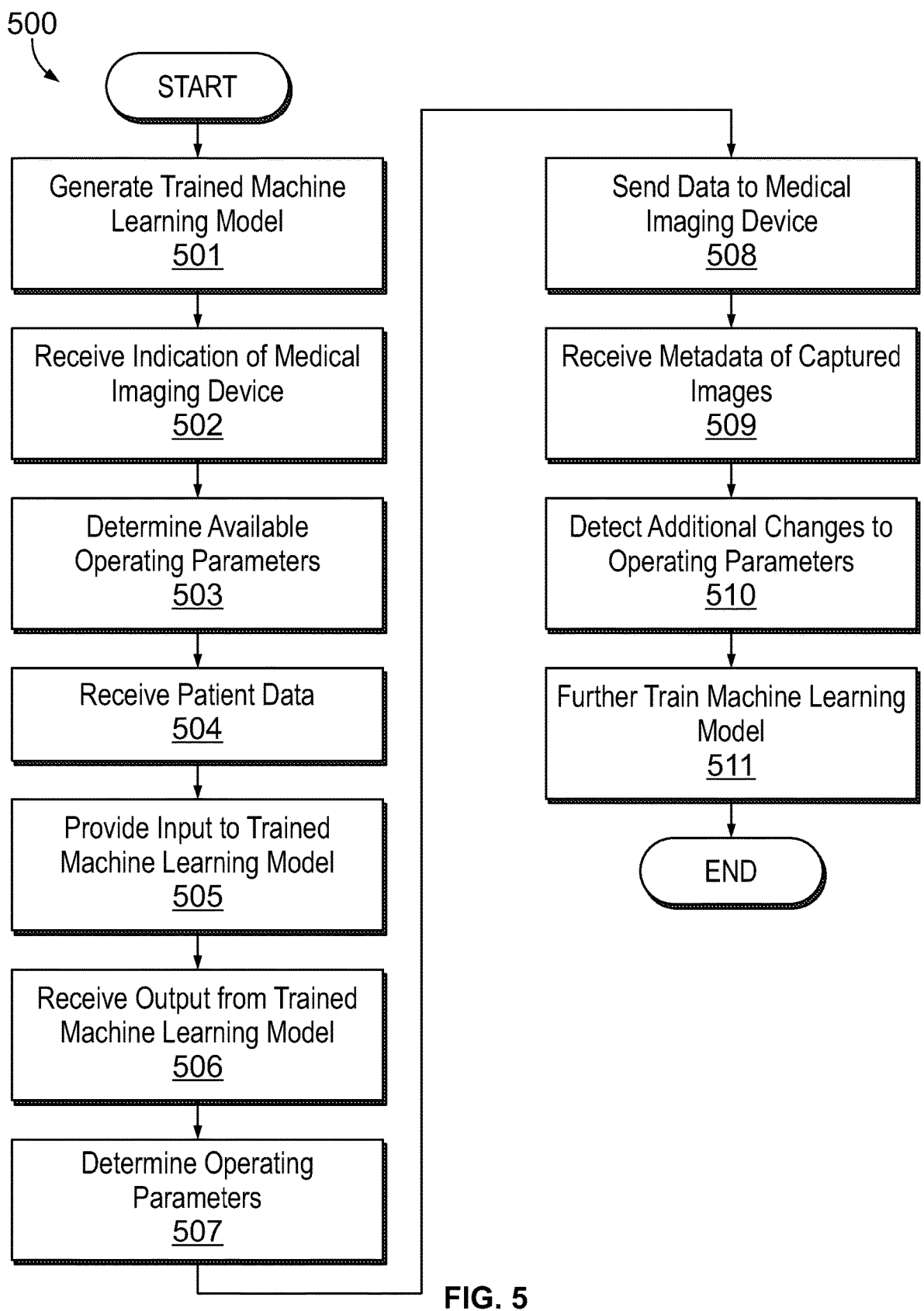
FIG. 5 depicts a flow chart with steps for using machine learning techniques to optimize medical imaging processes.

FIG. 5 depicts a flow chart depicting a method 500 comprising steps which may be performed by a computing device, such as the medical imaging device control system 301. A computing device may comprise one or more processors and memory storing instructions that, when executed by the one or more processors, cause performance of one or more of the steps of FIG. 5. One or more non-transitory computer-readable media may store instructions that, when executed by one or more processors of a computing device, cause the computing device to perform one or more of the steps of FIG. 5. Additionally and/or alternatively, one or more of the devices depicted in FIG. 3, such as the one or more medical imaging devices 302 and/or the one or more user devices 304, may be configured to perform one or more of the steps of FIG. 5. For simplicity, the steps below will be described as being performed by a single computing device; however, this is merely for simplicity, and any of the below-referenced steps may be performed by a wide variety of computing devices, including multiple computing devices.

In step 501, the computing device may generate the trained machine learning model. The trained machine learning model may be generated by training an artificial neural network, such as the one described with respect to FIG. 2. Such training might use training data relating to medical imaging device use. For example, the computing device may generate a trained machine learning model by training, using training data comprising a history of medical imaging device operating parameter settings, patient data, and imaging results, a machine learning model to output recommended medical imaging device operating parameter settings. As part of training the machine learning model, the computing device may modify, based on the training data, one or more weights of one or more nodes of an artificial neural network.

The training data may comprise a variety of data entries that correlate information about medical imaging device operating parameter settings (e.g., power settings, exposure settings), patient data (e.g., the type of patient imaged) and imaging results (e.g., one or more indicators of the quality of the image captured). In this way, the training data may thereby indicate which operating parameters resulted in useful images for particular patients. The fidelity and availability of the data might vary: for example, some data entries might miss certain portions of information (e.g., certain information about a patient), whereas others might use different units. Along those lines, training data may be pre-processed to, for example, ensure that units are consistent, that entries with missing data are remediated (e.g., removed, the missing data is estimated based on averages of other similar data entries, or the like). Moreover, the information about the imaging results may vary widely: some sets of training data might merely indicate of the images were used (e.g., were decent enough to be used by a doctor for the purposes of evaluation), whereas others might indicate particular measurements of image fidelity (e.g., using one or more image quality algorithms). A high-level example of such training data is provided below as Table 3. In the table below, the metric system is used. However, the system can also be designed to use inches and pounds and achieve similar results.

TABLE 3

| Operating Parameter Setting | Patient Height | Patient Weight | Imaging Results- Image(s) Good? |
| --- | --- | --- | --- |
| Continuous Imaging | 160 cm | 50 kg | Y |
| Pulse Imaging | 173 cm | 60 kg | Y |
| Continuous Imaging | 181 cm | Not Available | N |
| Pulse Imaging | 190 cm | 90 kg | N |

By way of further example, a substantial amount of the data used during the development of the present disclosure came from approximately five years of work in radiology and training for such radiology.

In step 502, the computing device may receive an indication of a medical imaging device. The indication of the medical imaging device may comprise any identifier of a medical imaging device, such as a serial number, a nickname, a model identifier, a manufacturer name, or the like. For example, the identifier may be "7000 R," designating the Philips Fluoroscopy 7000 R fluoroscopy system made by Koninklijke Philips N.V. of Amsterdam, the Netherlands. As another example, the identifier may be "Office 2," designating a particular x-ray machine located in a second office. As another example, the information concerning the medical device can relate to the quality of the machine being used for the procedure (e.g., A quality, B quality, C quality, or D quality). The quality of the machine can then be factored into the election of operating parameters, as adjustments may need to made to account for differences in the device being use. Such information may be provided via a user interface, such as might be displayed by the interface application 305 of the one or more user devices 304. An example of such an interface is discussed below with respect to FIG. 6A.

In step 503, the computing device may determine available operating parameters. This process may comprise looking up available operating parameters for a medical imaging device based on the medical imaging device indication received in step 502. For example, the computing device may determine, based on the indication of the medical imaging device, available operating parameters of the medical imaging device. Along those lines, determining the available operating parameters may entail querying a database, such as the one or more device information databases 303. For example, the computing device may query, based on the indication of the medical imaging device, a database of device identifications and corresponding operating parameters.

In step 504, the computing device may receive patient data. The patient data may comprise any information about a subject to be imaged, including but not limited to their height, weight, sex, the location of their body to be imaged, whether they have implants, their body composition (e.g., how muscular their body is), known ailments of the patient, or the like. This process may entail receipt, via a user interface, of the patient data. For example, the computing device may cause display, via a user device, of a user interface and then receive, via the user interface, a patient weight and a patient height. An example of such an interface is discussed below with respect to FIG. 6B.

One particularly important aspect of patient data relates to the overall density of the patient, which might be evinced by patient height, weight, the presence of prosthetics, and the like. Testing of the present disclosure reveals that certain conditions (e.g., osteopenia, osteoporosis, the presence of prosthetics) have a significant impact on the ability of medical imaging devices to image properly. In turn, such information might be included in the patient data because (as will be described below) it might be used to determine operating parameters.

In step 505, the computing device may provide input to the trained machine learning model. The input may comprise any of the data detailed above, including but not limited to the indication of the medical imaging device received in step 502, the available operating parameters determined in step 503, and/or the patient data received in step 504. For example, the computing device may provide, to one or more input nodes of the trained machine learning model, the patient data and data corresponding to the available operating parameters of the medical imaging device.

In step 506, the computing device may receive output from the trained machine learning model. The output may pertain to recommended operating parameter settings for the medical imaging device identified in step 502. For example, the computing device may receive, via one or more output nodes of the trained machine learning model, one or more recommended operating parameter settings. Such recommended operating parameter settings might be recommended settings for all or portions of a medical imaging device, such as recommended power settings, recommended exposure settings, recommendations relating to use of continuous and/or pulse settings, or the like.

The output of the trained machine learning model might not be a complete set of operating parameters for the medical imaging device. For example, based on the scope of the training data provided as part of step 501, the trained machine learning model may be configured to determine optimal operating parameters for the exposure of a medical imaging device, but not necessarily other optimal operating parameters for the medical imaging device. As such, the output of the trained machine learning model might not be immediately usable to instruct a medical imaging device to take an optimal image. This is one of the reasons for step 507, discussed below.

In step 507, the computing device may determine operating parameters. Determining the operating parameters may comprise predicting optimal operating parameters based on a variety of factors, such as the output of the trained machine learning model and/or the output of additional formulas and/or algorithms. For example, the computing device may determine the data (that is, the data to be transmitted to the medical imaging device to cause it to modify its operating parameters) based on the patient data and the one or more recommended operating parameter settings output by the trained machine learning model. As a particular example, the computing device might compare the output of the trained machine learning model and algorithmically-determined operating parameters (determined based on the patient data and/or information about the medical imaging device) to determine a combined set of operating parameters.

As part of step 507, the computing device may use one or more algorithms to account for patient variability when determining operating parameters. For instance, the output of the trained machine learning model may provide recommendations for some, but not all, operating parameters. In such a circumstance, the computing device may use an equation to determine certain operating parameters. Such an algorithm might rely on a calculation based on a comparison of different patient body features to ultimately derive an Equalizing Quotient (EQ). Such an EQ might be calculated as follows:

$$EQ = \frac{X(\text{Weight}_{pounds\ or\ kg})}{\text{Height}_{Inches\ or\ cm}}$$

In the formula above, X can be 1-10, preferably less than 4, and most preferably in the range of 1-3. This approach provides each patient a specific EQ that allows uses of predetermined graphs to pick out certain operating parameters. For instance, the EQ might be used to determine operating parameters for particular images (e.g., lateral images, oblique images) based on assumptions about the patient based on their body composition (e.g., whether they are thin, obese, muscular, or the like), with adjustments based on various measurements (e.g., abdomen offsets and hip offsets) and preexisting conditions (e.g., osteopenia, osteoporosis). Table 4 below shows the application of the EQ in real measurements for an anterior-posterior imaging view of the $4^{th}$ thoracic vertebrae. For example, a patient with a determined EQ of 4 would require technical settings of 94 kVp and 2.2 mAs to be applied.

TABLE 4

| EQ Scale | kVp | mAs |
|---|---|---|
| 2 | 88 | 1.8 |
| 3 | 91 | 2.00 |
| 4 | 94 | 2.20 |
| 5 | 97 | 2.50 |
| 6 | 100 | 2.70 |
| 7 | 103 | 3.00 |
| 8 | 107 | 3.50 |
| 9 | 111 | 4.10 |

Figure 8:
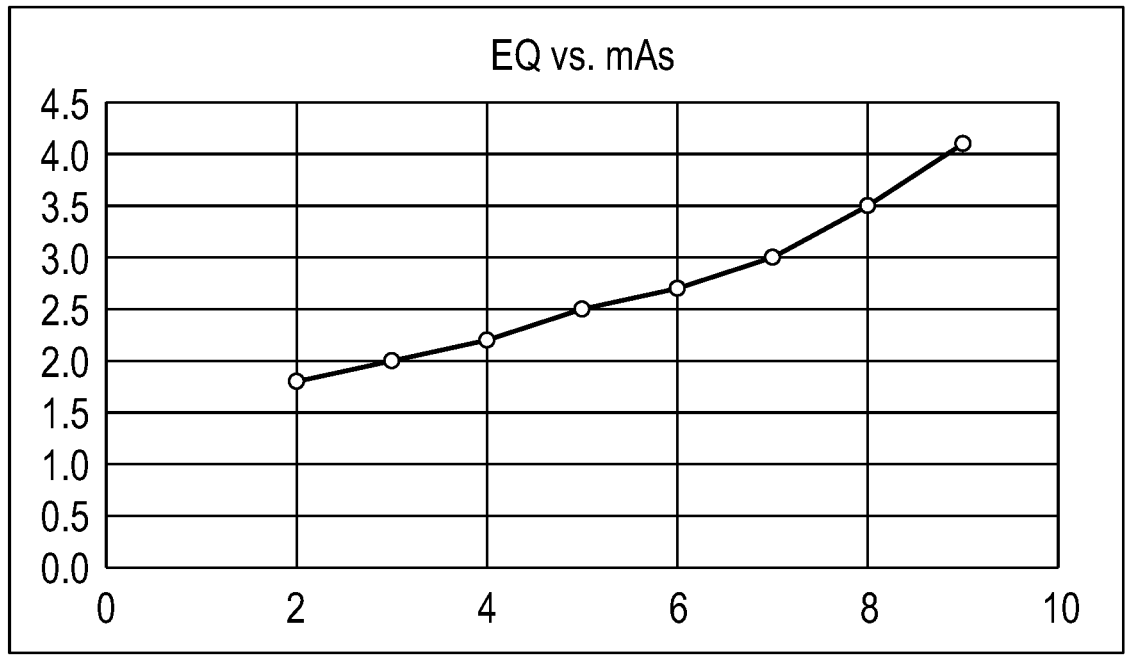
FIG. 8 shows equalizing quotient versus milliampere-seconds (mAs).
Figure 9:
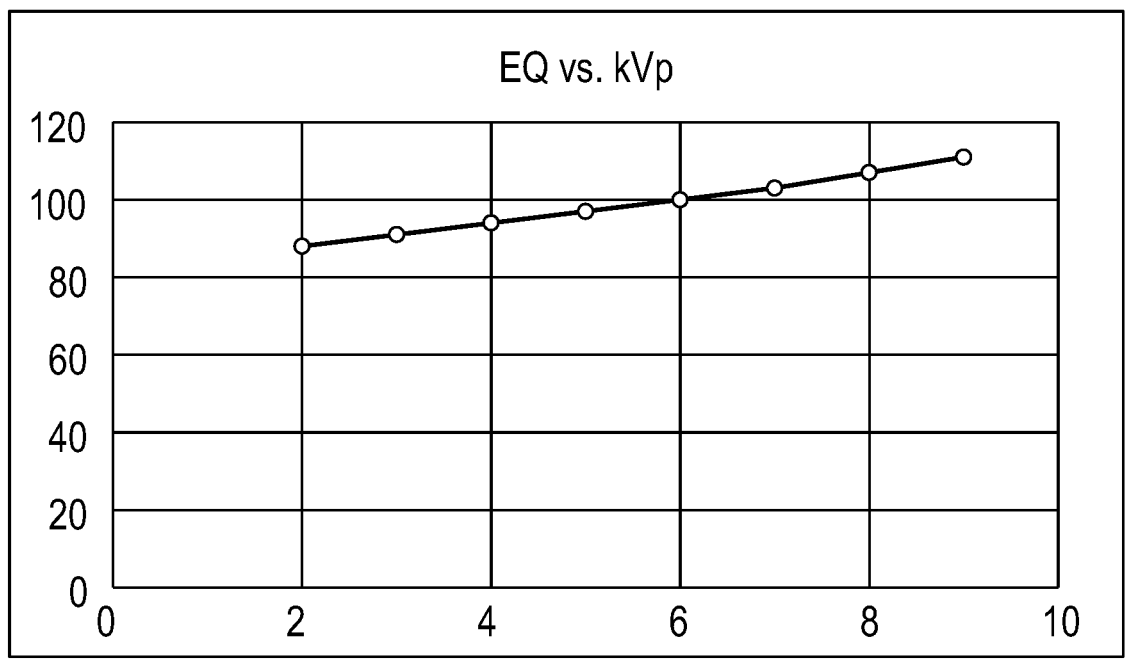
FIG. 9 shows equalizing quotient versus kilovoltage peak (kVp).
Figure 10:
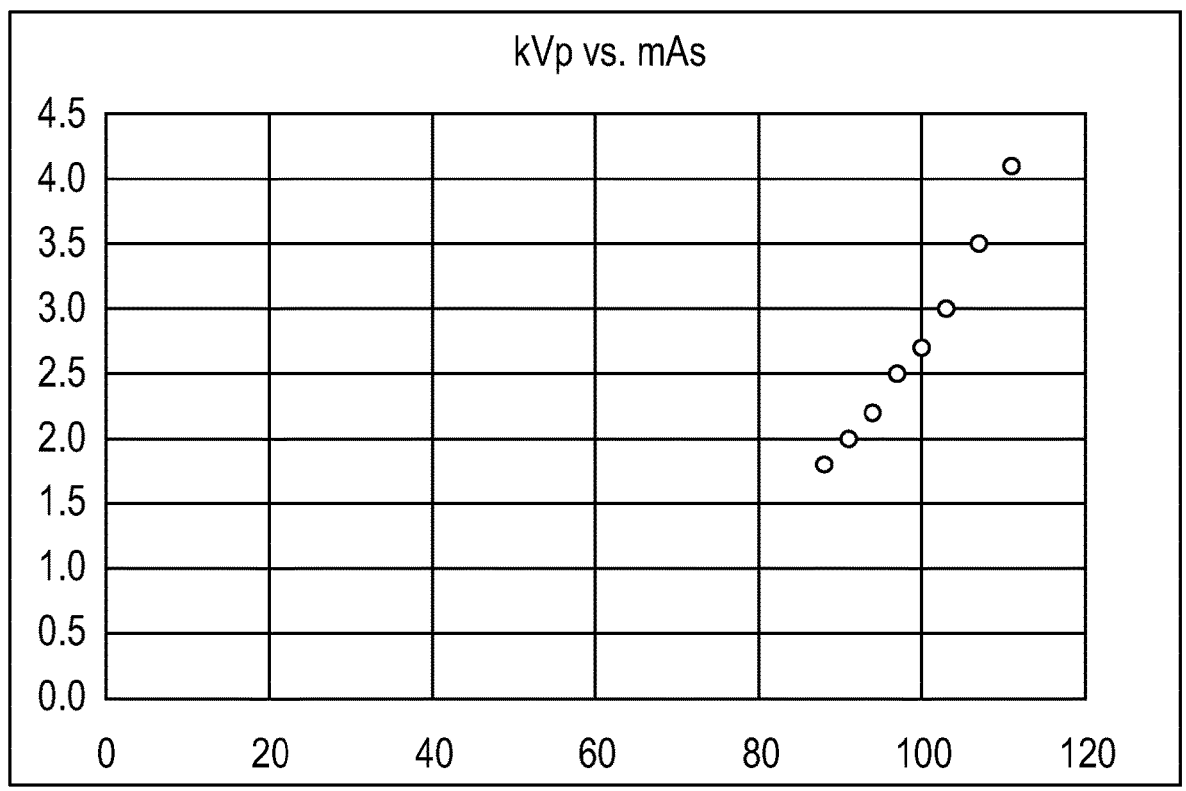
FIG. 10 shows kilovoltage peak versus milliampere-seconds.

FIGS. 8-10 generally show the correlative relationship the inventors determined can exist between EQ, kVp, and mAs. The graphs in FIGS. 8A-8C define a curve and its slope as it applies to the relationship between an EQ and kVp, EQ and mAs, and the relationship between kVp, and mAs for each EQ. Although the data in Table 4, and relationships illustrated in FIGS. 8-10, were generated for an anterior-posterior imaging view of the 4th thoracic vertebrae, these same principles can be applied to individual or grouped levels of the spine, components of the extremities, the chest and its parts and levels, the abdomen and its parts and levels, the trunk and its parts and its levels. Even though the aforementioned locations are distinct targets, using the data and information provided herein, a person skilled in the art can apply the same EQ techniques described based on known adjustments and imaging.

That said, use of such an EQ can also be a starting point, and additional patient data may be taken into consideration by the algorithm as well. For example, a patient's body mass index ("BMI") could be used alone or together with the algorithm to derive an EQ. BMI is calculated by the following formula: weight (kg)/height (m2). BMI can alternatively be calculated by using weight (lbs)/height (in2), which is then multiplied by 703. In another example, an image capture device can be used to take a patient image or silhouette which is then used to approximate the size and body type of a particular patient. In addition, patients with implants might be treated differently than patients without implants. Moreover, and as already suggested above, modifying factors (e.g., fat versus bone versus muscle versus prosthetic hardware density) might require modification of such calculations. Such modifying factors might be determined by radiology technologists and doctors based on experience with such cases: for example, the algorithm might learn to weight the EQ in a certain way if a patient has a prosthetic device. After all, such considerations have a direct implication for radiation penetration and strength.

In turn, the computing device may use the EQ for the purposes of determining the data configured to cause modification of operating parameters. For example, the computing device may, as part of transmitting the data that causes modification of the operating parameters of the medical imaging device, determine an EQ, wherein the EQ is calculated by phi X by the weight of the patient, wherein X is between 1-10, preferably less than 4, and most preferably between 1-3 to obtain a product, and then dividing the product by the height of the patient, and then determine the data by modifying the one or more recommended operating parameter settings based on the EQ. One of the benefits of using the algorithm described herein is that AEC can be disabled before any images are generated, thus significantly lowering radiation exposure of the procedure to the patient, doctor, radiology technologist, and staff. AEC is designed to be a safety feature to lower radiation exposure on x-ray devices. However, the inventors counterintuitively discovered, as a result of their years of study, that generating operating parameters based on patient and procedure specific information, and deactivating AEC, actually yields lower radiation exposure.

Examples of the type of operating parameters that might be determined are provided below in Table 5, which represents anonymized versions of real operating parameters determined for a 65-inch male having an average build during testing of the present disclosure.

TABLE 5

| | Anterior Posterior (AP) View | | Oblique View | | Lateral View | |
|---|---|---|---|---|---|---|
| | kVp | mAs | kVp | mAs | kVp | mAs |
| Lumbar Spine | 100 | 4.7 | 103 | 5.0 | 114 | 6.3 |
| Upper Extremity, Shoulder | 78 | 2.7 | 81 | 3.0 | 78 | 2.7 |

For all of these results, the EQ (derived using the formula above) was 6.15, automatic exposure control was set to disabled, auto contrast was set to on, and pulse imaging was enabled. In contrast, images taken without the benefit of these predetermined settings were very visibly washed out (e.g., very white looking or dark and indiscernible), which would have required additional imaging (and thus additional radiation exposure for all involved).

In addition to the patient-related variations discussed above, medical imaging device-related variations may also be considered. For example, as discussed above with respect to FIG. 3, different medical imaging devices might behave differently based on tube age, the years they have been in service, and the like. Such information might be stored and/or monitored by the one or more device information databases 303. In turn, such information might be considered (e.g., via the algorithm described above, and/or provided as input to the trained machine learning model as part of step 505) to ensure that such variations are considered when operating parameters are selected.

In step 508, the computing device may send data to the medical imaging device. For example, the computing device may transmit, to the medical imaging device, data that causes modification of operating parameters of the medical imaging device based on the one or more recommended operating parameter settings. The data may cause the medical imaging device to capture images in a variety of ways. For example, the data may be configured to cause the medical imaging device to set an auto feature off and capture a sequence of images at a predetermined frequency (as described below). As another example, the data may be configured to cause the medical imaging device to disable an automatic exposure control setting.

The data may cause the medical imaging device to modify a variety of operating parameters. Take, for example, the "Auto" feature on many imaging devices. The Auto feature is, generally speaking, industry-standard automatic exposure control. This feature generally uses radiation exposure to measure the contrast detection to determine the best quality image. In other words, this use of continuous images allows the medical imaging device to meet a defined threshold of exposure to achieve the intended image quality. While this process might have a lower dose rate in the moment, the duration is dramatically longer and overall will increase the exposure and thus scatter radiation. As such, the data might cause the medical imaging device to disable Auto in some circumstances. Take, as another example, the pulse feature. In some medical imaging devices, imaging is performed using continuous and/or pulse imaging. With continuous imaging, radiation may be continuously produced until the exposure button is released. In contrast, in a pulse mode, the radiation is produced in defined pulses (often 8 pulses per second). The pulsing feature might be used, as testing suggests that it can produce high-quality images without requiring excessive use of radiation.

The data sent to the medical imaging device may cause the medical imaging device to perform staccato-style imaging. For example, fluoroscopy devices may perform static or live imaging. Staccato mode imaging is intended to replace live mode. Live fluoroscopy is typically done in auto settings with pulse rate set at 8 pulses per second. This increases radiation exposure significantly. With staccato mode data sent in step 508 may instruct the medical imaging device to disable an automatic imaging feature and use pulse mode such that the pulse rate remains at 8 or 4 pulses per second. However, the pulse mode is turned on and staccato style imaging will deliver these pulse images at 1 exposure per second, 2 exposures per second, 3 exposures per second or 4 exposures per second. By utilizing pulse mode with auto features off with predetermined settings, the scatter radiation and radiation exposure is reduced, but the image quality remains high.

In step 509, the computing device may receive metadata of images captured by the medical imaging device. The metadata may comprise any information about the medical imaging device before, during, or after capture of one or more images. For example, the computing device may receive metadata corresponding to one or more images captured by the medical imaging device. The metadata may be usable to determine a quality of the images (e.g., whether they are sufficiently clear), a duration of radiation used to capture the images, the number of images captured, whether one or more images were discarded, whether one or more images were saved and/or otherwise approved, or the like.

Determining the metadata may entail use of image quality algorithms, such as Histogram, digital subtraction to enhance fat elimination in an image. Various algorithms have been developed for determining image quality, and any of those algorithms may be used (alone or in combination) to determine all or portions of the metadata. For example, the computing device may determine the metadata by processing the one or more images to identify an image quality for each of the one or more images. As a simple example, an algorithm may be used to process the one or more images to determine whether lines appear sufficiently sharp, and a score might be determined based on the sharpness of the lines. That score might then be usable to, as will be described below, further train the trained machine learning model.

The metadata may comprise any information about the operating parameters of the medical imaging device before, during, or after image capture. For example, the metadata may relate to a quantity of one or more images captured by the medical imaging device, whether a pulse setting was activated during capture of the one or more images, and/or whether an auto setting was activated during capture of the one or more images.

In step 510, the computing device may detect additional changes to operating parameters of the medical imaging device. To perform this process, the computing device may monitor the medical imaging device to see if the operating parameters were further modified (e.g., by a radiology technologist) to improve image quality. In turn, such adjustments might indicate opportunities to define more precise settings on the part of the trained machine learning model, and may merit further training of the trained machine learning model. For example, the computing device may determine one or more further modifications made to the operating parameters of the medical imaging device and then, based on the one or more further modifications, further train the trained machine learning model.

In step 511, the computing device may further train the trained machine learning model. The trained machine learning model may be further trained based on, for example, the metadata received in step 509 and/or the additional changes detected in step 510. For example, the computing device may further train, based on the metadata, the trained machine learning model. This process ensures that the trained machine learning model continues to learn over time, improving its ability to recommend operating parameters by, for example, learning circumstances where its output in step 506 was insufficient for the purposes of generating high-quality images.

As an example of how the process depicted in FIG. 5 might operate, a radiology technologist might login to a user interface (e.g., via the interface application 305 executing on the one or more user devices 304) and may, as part of step 502, provide some indication of a medical imaging device, such as its nickname, its model number, its manufacture date, its model type, its hours of service, its serial number, or the like. The technologist may, as part of step 504, additionally provide information such as an imaging specialty type and patient data such as the patient's height, weight, age, body composition, sex, special considerations (e.g., osteopenia, osteoporosis, prosthetic devices), and the like. The data may also specify the view to be utilized (e.g., oblique, lateral, anterior posterior). The computing device may then, as part of step 505, provide that data as input to a trained machine learning model and additionally and/or alternatively use such data as input to various algorithms. The output of the trained machine learning model and/or the output of the algorithms may, as part of step 507, be compared, and the computing device might ultimately determine recommended operating parameters for a medical imaging device. Those recommended operating parameters might be provided to the medical imaging device as part of step 508, and the medical imaging device might capture one or more images as instructed (e.g., by taking a static image, using a pulse mode, using a process that disables auto settings, or the like). The image quality may be evaluated as part of step 509 (e.g., to determine whether it is too light, too dark, too grainy, or the like). The operating parameters might be then further modified as part of step 510, and additional images might be captured. Metadata about the images and/or further modifications by the radiology technologist might be used to further train (and thereby improve) the trained machine learning model as part of step 511.

FIG. 6A through FIG. 6J show various illustrative user interfaces which may be output by the interface application 305 of the one or more user devices 304. These user interfaces may be used as part of, for example, receiving the indication of the medical imaging device in step 502, receiving the patient data in step 504, receiving additional changes to operating parameters as part of step 510, or the like. As will be discussed below, these user interfaces may be displayed before imaging (e.g., to collect patient data and/or to allow users to modify operating parameters recommended by the trained machine learning model before imaging begins) and/or during/after imaging (e.g., to allow users to modify operating parameters for subsequent rounds of imaging).

Figure 6B:
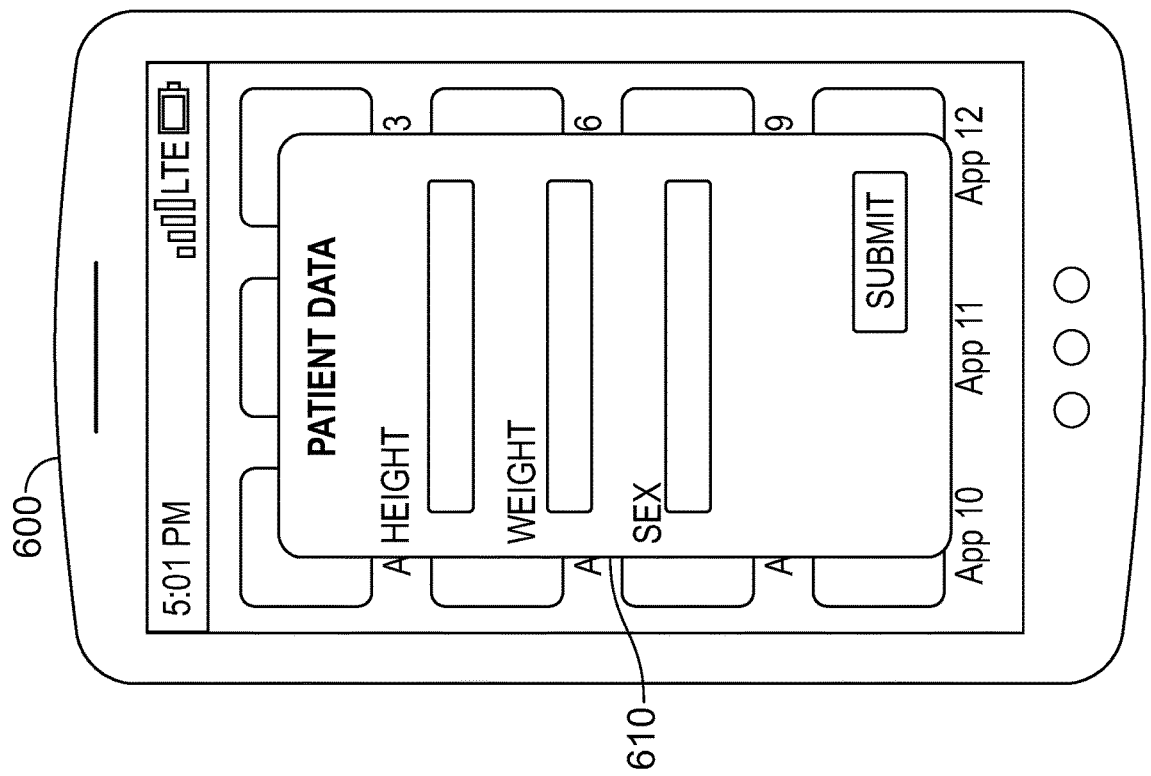
FIG. 6B shows a mobile device outputting a patient data entry user interface.
Figure 6A:
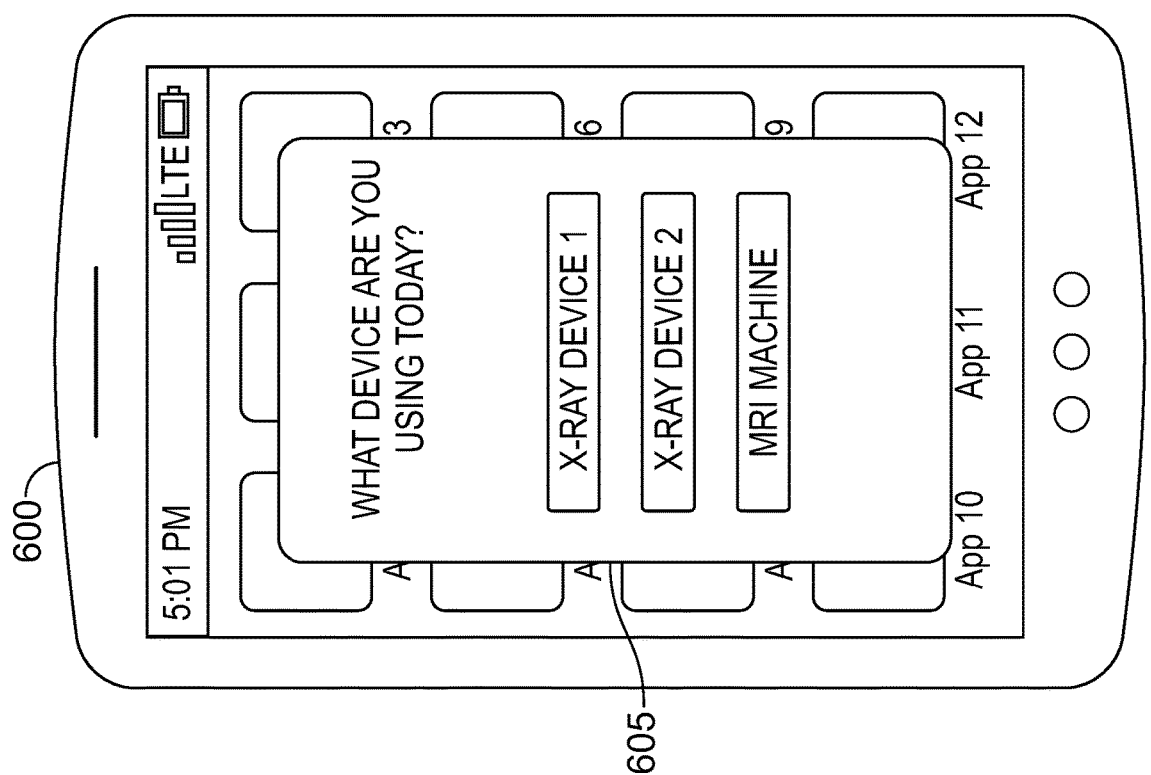
FIG. 6A shows an example of a mobile device outputting a medical imaging device selection user interface.

FIG. 6A shows an example of a mobile device 600 (which may be the same or similar as the one or more user devices 304) showing a medical imaging device selection user interface 610 (which may be displayed via the interface application 305). The medical imaging device selection user interface 610 may, as shown in FIG. 6, enable a user to provide an indication of a medical imaging device. For example, a user might indicate whether they are using a first fluoroscopy device, a second fluoroscopy device, or general radiography, including, but not limited to portable radiography, plain film, digital radiography (DR), computed radiography (CR) and tomography. Such an input might be received as, for example, part of step 502 of FIG. 5.

FIG. 6B shows the mobile device 600 showing a patient data entry user interface 620 (which may be displayed via the interface application 305). The patient data entry user interface 620 may permit a user to enter data about a patient to be imaged, such as their height, weight, and sex. Additional patient data might be entered as well, such as the region of the body to be imaged, the body composition of the patient (e.g., whether they are particularly muscular), whether the patient has implants, the patient's bone density (e.g., normal, osteopenia, osteoporosis), or the like. All or portions of such information might be used as patient data in, for example, step 504 of FIG. 5.

Figure 6D:
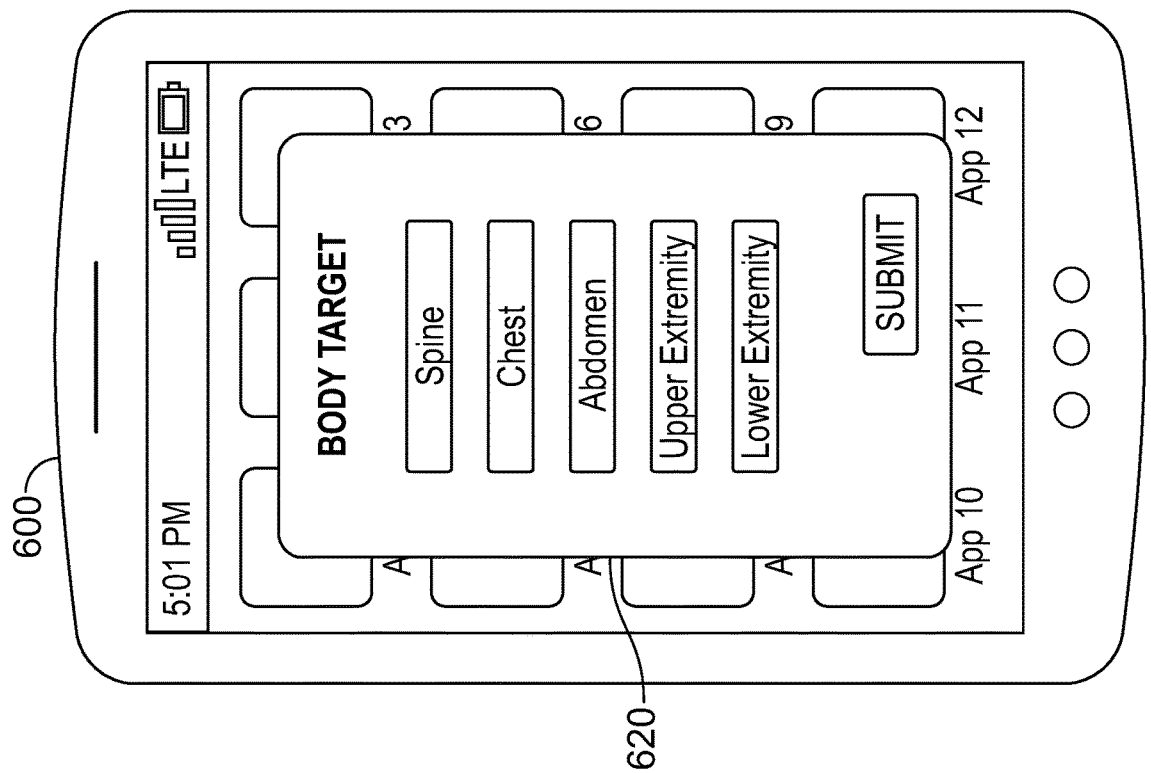
FIG. 6D shows a mobile device outputting a body target selection user interface.
Figure 6C:
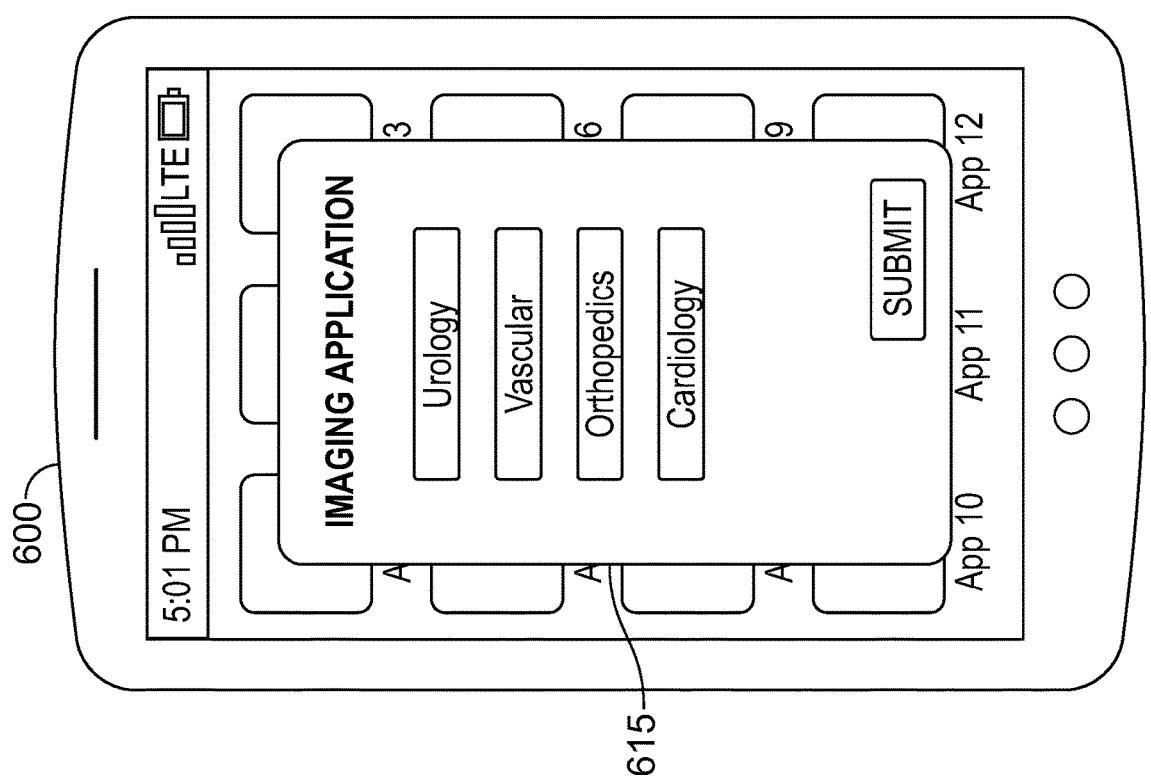
FIG. 6C shows a mobile device outputting an imaging application selection user interface.
Figure 6F:
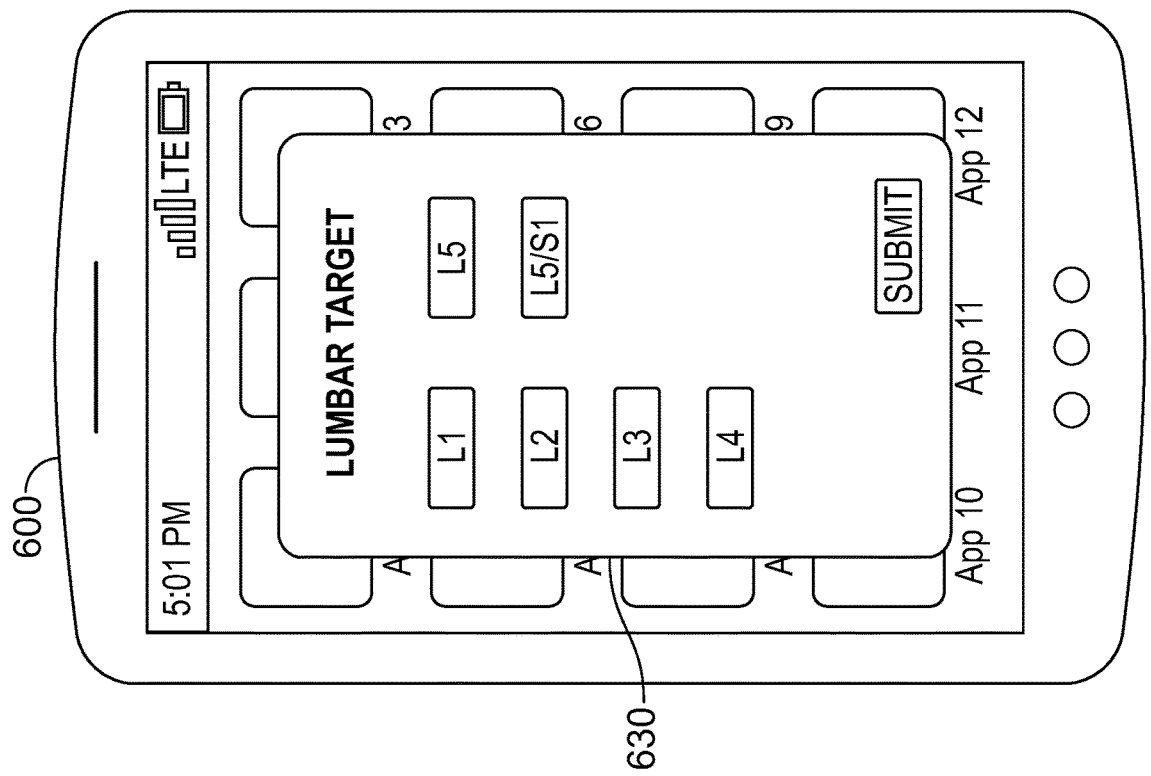
FIG. 6F shows a mobile device outputting a lumbar target selection user interface.
Figure 6E:
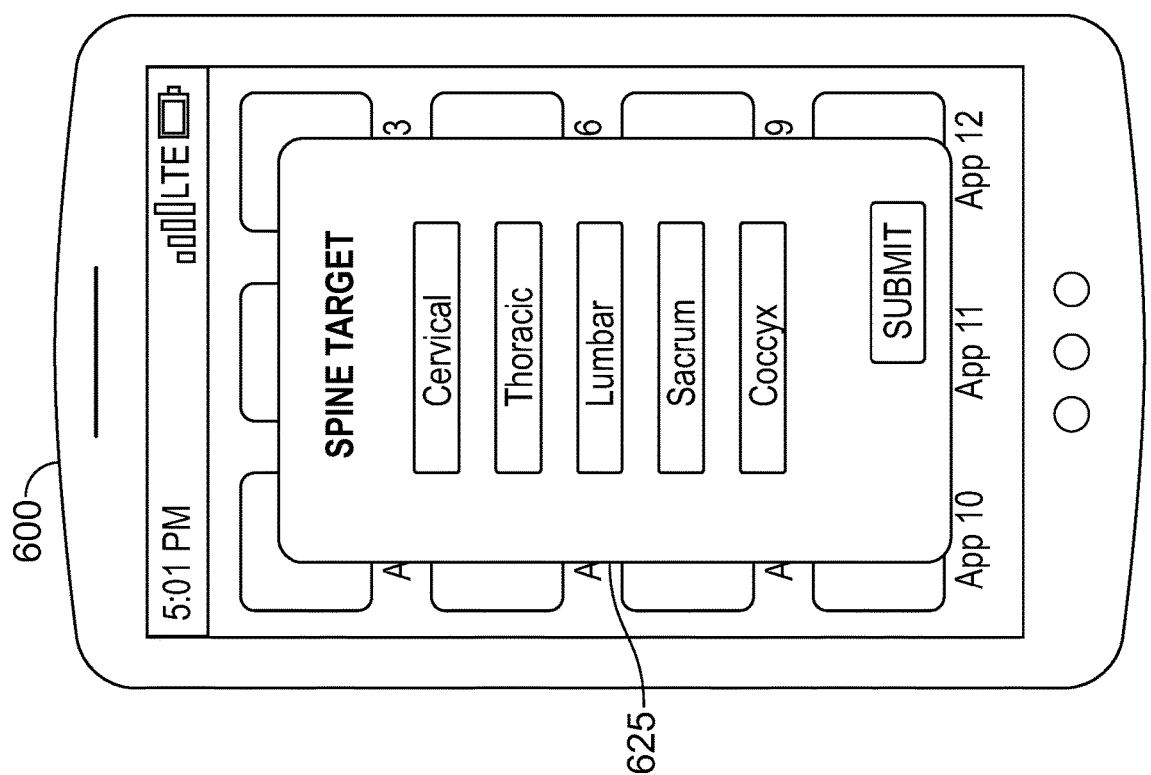
FIG. 6E shows a mobile device outputting a spine target selection user interface.

As an introduction to FIG. 6C, FIG. 6D, and FIG. 6E, a user might provide information about a patient, such as what portions of their body are being scanned. In the case depicted in those figures, this information might be provided through a multi-step menu, whereby the user first selects an application for imaging (e.g., a department of a hospital or a gastroenterologist could specify digital subtraction after first image to remove fat), with subsequent menus further drilling down into a particular portion of the patient's body.

FIG. 6C shows the mobile device 600 outputting an imaging application selection user interface 615. The imaging application selection user interface 615 may allow a user to select a category of scanning topics, such has urology, vascular, orthopedics, or cardiology. Selection of any of these options might reveal further menus, as discussed below with respect to FIG. 6D. Any entry in the imaging application selection user interface 615 may additionally and/or alternatively be included as part of the patient data received in step 504.

FIG. 6D shows the mobile device 600 outputting a body target selection user interface 620. This menu may be presented responsive to a user selecting one of the options depicted in the imaging application selection user interface 615 of FIG. 6C. Particularly, the body target selection user interface 620 allows a user to select from body parts such as the spine, the chest, the abdomen, the upper extremities, and the lower extremities. Selection of any of these options might reveal further menus, as discussed below with respect to FIG. 6E. Any entry in the body target selection user interface 620 may additionally and/or alternatively be included as part of the patient data received in step 504.

FIG. 6E shows the mobile device 600 outputting a spine target selection user interface 625. The spine target selection user interface 625 might be shown responsive to a user selecting the spine option of the body target selection user interface 620 of FIG. 6D. In the circumstance depicted in FIG. 6E, the spine target selection user interface 625 may allow a user to select from options such as cervical, thoracic, lumbar, sacrum, or coccyx. Selection of any of these options might reveal further menus, as discussed below with respect to FIG. 6F. Any entry in the spine target selection user interface 625 may additionally and/or alternatively be included as part of the patient data received in step 504.

FIG. 6F shows the mobile device 600 outputting a lumbar target selection user interface 630. The lumbar target selection user interface 630 may be displayed responsive to a user selecting the lumbar option of the spine target selection user interface 625 of FIG. 6E. In the circumstance depicted in FIG. 6F, the lumbar target selection user interface 630 may allow a user to select from options such as L1, L2, L3, L4, L5, and/or L5/S1. Any entry in the lumbar target selection user interface 630 may be included as part of the patient data received in step 504.

Figure 6H:
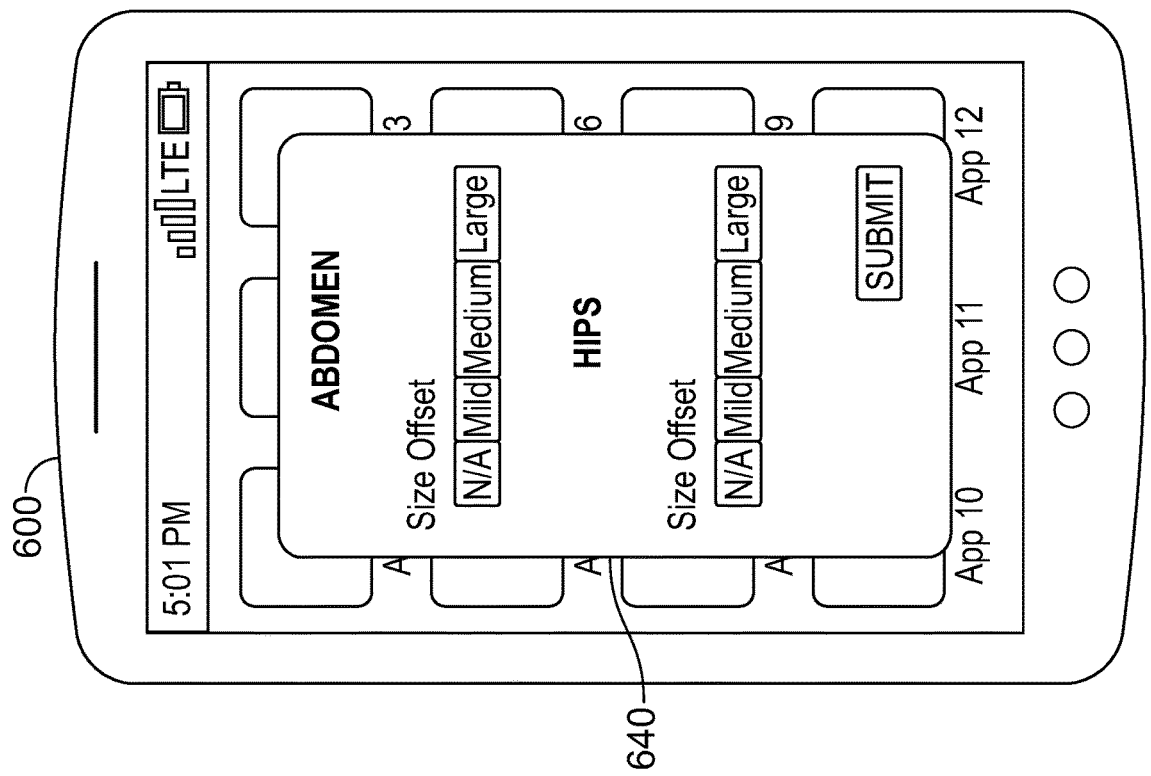
FIG. 6H shows a mobile device outputting an abdomen and hip offset selection user interface.
Figure 6G:
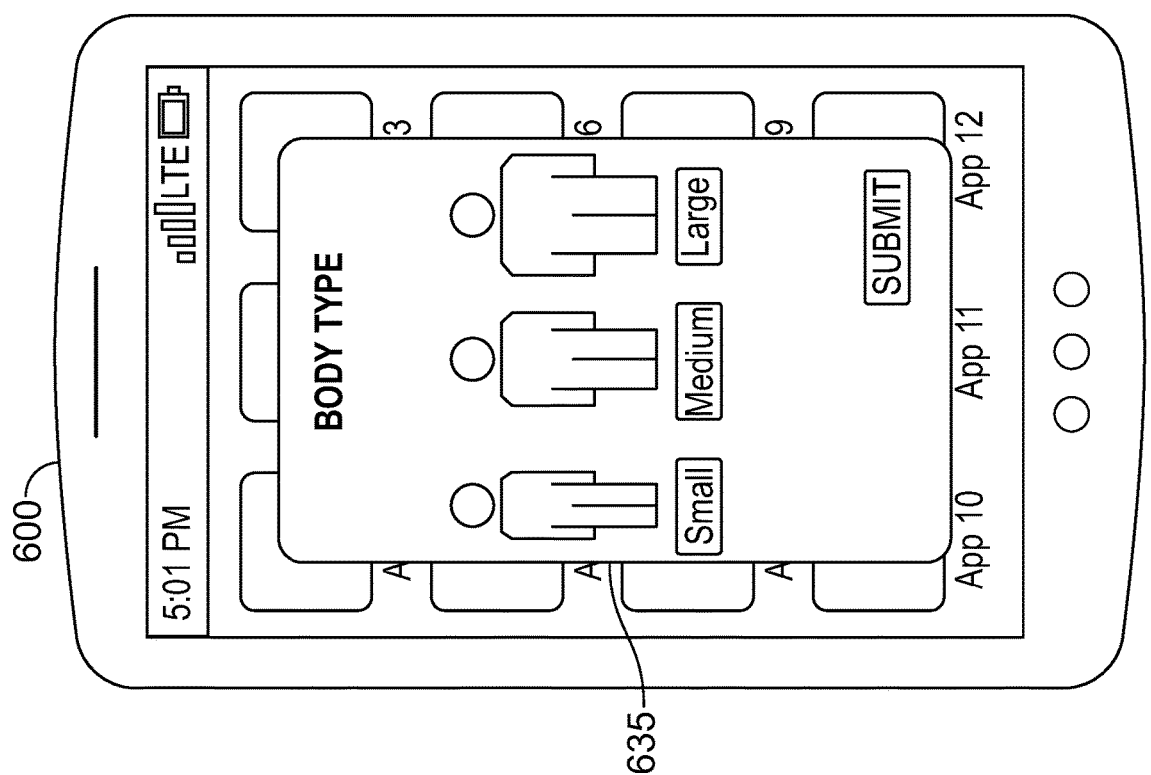
FIG. 6G shows a mobile device outputting a body type selection user interface.

FIG. 6G shows the mobile device 600 outputting a body type selection user interface 635. The body type selection user interface 635 allows a user to select from a variety of body composition types for a patient. This body type selection user interface 635 may be useful because different body types (e.g., particularly thin and/or muscular body types) may require different types of imaging, such as a greater or weaker strength of radiation. In the circumstance depicted in FIG. 6G, the body type selection user interface 635 allows a user to select from options such as small, medium, and/or large. Any entry in the body type selection user interface 635 may be included as part of the patient data received in step 504.

FIG. 6H shows the mobile device 600 outputting an abdomen and hip offset selection user interface 640. For similar reasons as the body type selection user interface 635, various distributions of size in different body parts may require different approaches to imaging. For example, if a patient is very thin but has particularly large hips, this may require a different approach to imaging as compared to a patient who has relatively smaller hips. In turn, the body type selection user interface 635 permits a user to select information such as a size offset for the abdomen of the patient and a size offset for the hips of the patient. Of course, any portions of the patient may be offset in this manner, and the present disclosure is not limited to abdomen and hip offsets. Any entry in the body type selection user interface 635 may be included as part of the patient data received in step 504.

Figure 6J:
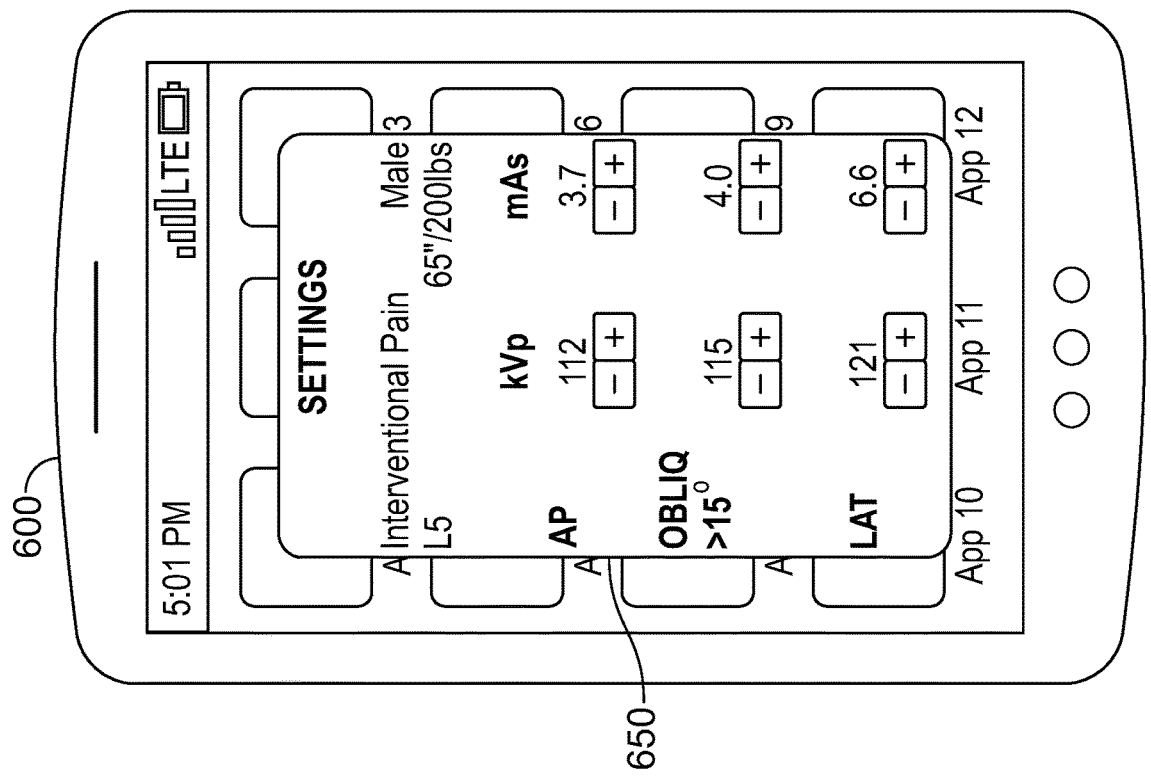
FIG. 6J shows a mobile device outputting a settings user interface.
Figure 6I:
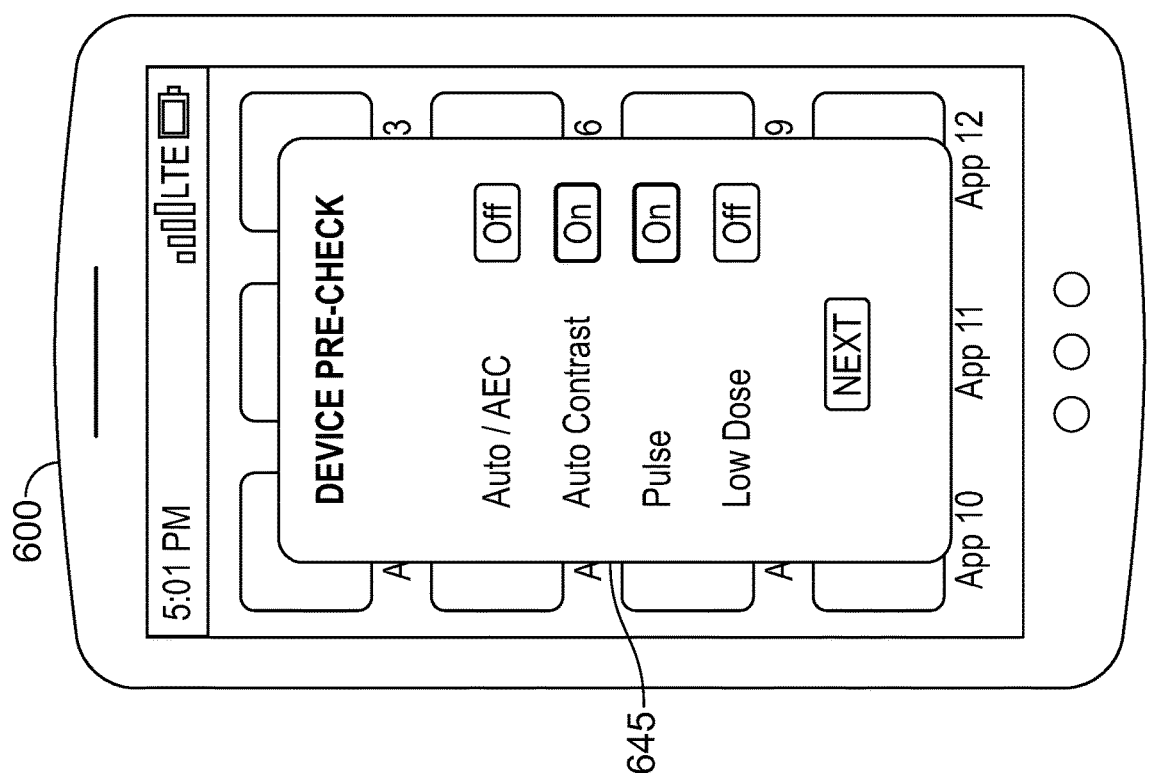
FIG. 6I shows a mobile device outputting a device pre-check user interface.

As an introduction to FIG. 6I and FIG. 6J, after operating parameters have been determined as part of step 507 of FIG. 5, the customized operating parameters tailored for the individual subject may be displayed, in whole or in part, via a user interface. This may be prior to imaging (e.g., such that a user can see the recommended operating parameters and adjust those parameters as desired before imaging begins), during imaging (e.g., to show the user what type of operating parameters are being used for the images currently being captured) and/or after imaging (e.g., such that the user can see what operating parameters were used and make further modifications for further imaging as desired).

FIG. 6I shows the mobile device 600 outputting a device pre-check user interface 645. In the example shown by FIG. 6I, the device pre-check user interface 645 shows that the operating parameters decided for imaging (e.g., as part of step 507 of FIG. 5) are configured such that AEC is turned off, auto contrast is turned on, a pulse setting is turned on, and a low dose setting is turned off. In the case where the device pre-check user interface 645 is displayed before imaging, a user might change these settings as desired, effectively overriding the decisions made by the computing device in part of step 507. In the case where the device pre-check user interface 645 is displayed during and/or after imaging, a user might change these settings for subsequent rounds of imaging.

FIG. 6J shows the mobile device 600 outputting a settings user interface 650. In the example shown by the settings user interface 650, the settings user interface 650 shows that the operating parameters decided for imaging (e.g., as part of step 507 of FIG. 5 and for a male patient that is 65" tall and 200 lbs having their L5 disc imaged) are configured such that an AP setting is set to 112 kVp and 3.7 mAs, an oblique setting is set to 115 kVp and 4.0 mAs, and a lateral setting is set to 120 kVp and 6.6 mAs. In the case where the settings user interface 650 is displayed before imaging, a user might change these settings as desired, effectively overriding the decisions made in part of step 507. In the case where the settings user interface 650 is displayed during and/or after imaging, a user might change these settings for subsequent rounds of imaging.

Discussion will now turn to additional approaches for optimizing imaging processes to reduce inadvertent exposure to harmful radiation. As part of and/or separate from the approaches described above, various algorithms and approaches may be used to determine optimized operating parameters. This includes, as already discussed above, the use of an EQ, or equalizing quotient, based on patient data.

Figure 7:
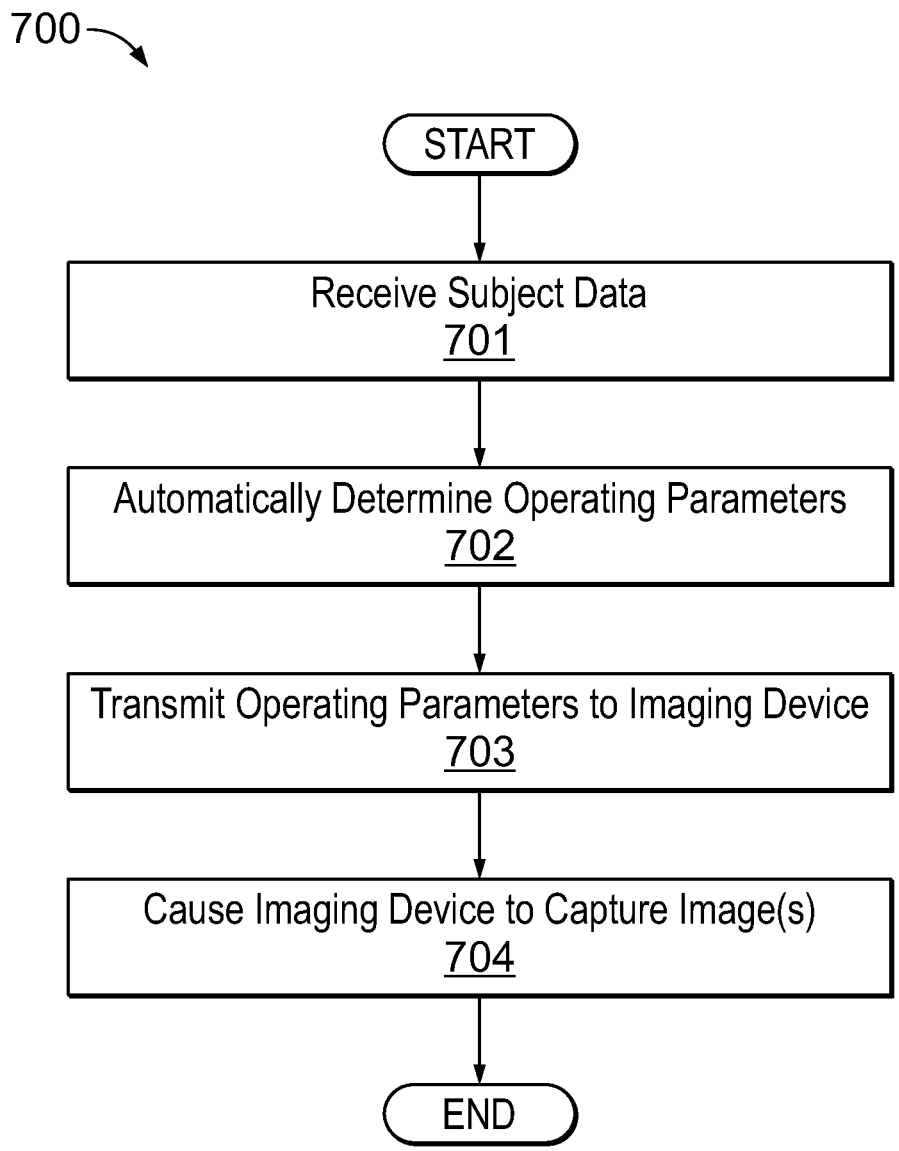
FIG. 7 depicts a flow chart with steps for optimizing imaging processes.

FIG. 7 depicts a flow chart depicting a method 700 comprising steps which may be performed by a computing device, such as the medical imaging device control system 301. A computing device may comprise one or more processors and memory storing instructions that, when executed by the one or more processors, cause performance of one or more of the steps of FIG. 7. One or more non-transitory computer-readable media may store instructions that, when executed by one or more processors of a computing device, cause the computing device to perform one or more of the steps of FIG. 7. Additionally and/or alternatively, one or more of the devices depicted in FIG. 3, such as the one or more medical imaging devices 302 and/or the one or more user devices 304, may be configured to perform one or more of the steps of FIG. 7. For simplicity, the steps below will be described as being performed by a single computing device; however, this is merely for simplicity, and any of the below-referenced steps may be performed by a wide variety of computing devices, including multiple computing devices.

In step 701, the computing device may receive subject data. This step may be the same or similar as step 504 of FIG. 5, though the term subject data is used to refer to the patient data. The data may comprise a variety of information about a subject, such as their weight, height, body composition, sex, existing ailments, or the like. For example, the computing device may receive, from a user device, subject data that comprises a weight of a subject and a height of the subject.

The computing device may receive subject data using a user interface. For example, the computing device may cause the user device to display a user interface and may receive, via the user interface, input data indicating the weight of a subject and the height of the subject. In some instances, multiple user interfaces may be displayed, such as one user interface for the purposes of collecting imaging device information and another for the purposes of collecting subject data. For example, the computing device may cause a user device to display a first user interface, receive, via the first user interface, an indication of an imaging device, and determine, based on the indication of the imaging device, available operating parameters of the imaging device. The computing device may then cause the user interface to display a second user interface and receive, via the second user interface, subject data such as a subject height, a subject weight, body composition data, and a target location of the subject. In addition, the system can be configured to include a parameter collection system, which includes a list of cases for a specific day, which would include, among other things, known subject data (e.g., patient height and weight) and image type.

In step 702, the computing device may automatically determine operating parameters for an imaging device, such as an x-ray device and/or a fluoroscopy device. This step may be the same or similar as step 507 of FIG. 5. This may involve determining the operating parameters using an algorithm and/or set of rules and based on the subject data received in step 701. For example, the computing device may automatically determine operating parameters, for an imaging device, configured to reduce radiation exposure based on a specific type of imaging procedure to be performed, a target location of the subject, and the subject data. The operating parameters may comprise parameters such as peak kilovoltage, tube current, and/or exposure time. The operating parameters may cause the imaging device to deactivate an automatic exposure control setting prior to generating an image.

As part of step 702, the computing device may determine an Equalizing Quotient (EQ). As described above, the equalizing quotient may be determined by, for example, multiplying X by the weight of the patient, wherein X is between 1-10, preferably less than 4, and most preferably between 1-3 to obtain a product, and then dividing the product by the height of the patient. In turn, the EQ may be used to modify operating parameters to account for variability in a subject. For example, the computing device may determine the operating parameters by using the EQ to determine the operating parameters.

In step 703, the computing device may transmit the operating parameters to the imaging device. This step may be the same or similar as step 508 of FIG. 5. In addition, the computing device can wirelessly transmit the parameters to a separate CPU board (not shown) contained within the imaging device. The use of a separate CPU board is particularly advantageous to retrofit older imaging devices to communicate with the computing device.

In step 704, the computing device may cause the imaging device to capture images based on the transmitted operating parameters. For example, the computing device may cause the imaging device to generate an image of the subject using the operating parameters by deactivating an automatic exposure control setting of the imaging device prior to generating the image.

The following paragraphs (M1) through (M16) describe examples of methods that may be implemented based on the present disclosure.

(M1) A method for using machine learning techniques to optimize medical imaging processes to reduce inadvertent exposure to harmful radiation, the method comprising: generating a trained machine learning model by training, using training data comprising a history of medical imaging device operating parameter settings, patient data, and imaging results, a machine learning model to output recommended medical imaging device operating parameter settings, wherein training the machine learning model comprises modifying, based on the training data, one or more weights of one or more nodes of an artificial neural network; receiving an indication of a medical imaging device; determining, based on the indication of the medical imaging device, available operating parameters of the medical imaging device; receiving patient data; providing, to one or more input nodes of the trained machine learning model, the patient data and data corresponding to the available operating parameters of the medical imaging device; receiving, via one or more output nodes of the trained machine learning model, one or more recommended operating parameter settings; transmitting, to the medical imaging device, data that causes modification of operating parameters of the medical imaging device based on the one or more recommended operating parameter settings; receiving metadata corresponding to one or more images captured by the medical imaging device; and further training, based on the metadata, the trained machine learning model.

(M2) The method of paragraph (M1), further comprising: determining one or more further modifications made to the operating parameters of the medical imaging device, wherein the further training the trained machine learning model is further based on the one or more further modifications.

(M3) The method of any one of paragraphs (M1)-(M2), wherein the receiving the metadata corresponding to one or more images captured by the medical imaging device comprises: determining the metadata by processing the one or more images to identify an image quality for each of the one or more images.

(M4) The method of any one of paragraphs (M1)-(M3), wherein transmitting the data that causes modification of the operating parameters of the medical imaging device comprises: determining the data based on: the patient data; and the one or more recommended operating parameter settings.

(M5) The method of any one of paragraphs (M1)-(M4), wherein the receiving the patient data comprises: causing display, via a user device, of a user interface; and receiving, via the user interface, a patient weight and a patient height.

(M6) The method of any one of paragraphs (M1)-(M5), wherein the determining the available operating parameters of the medical imaging device comprises: querying, based on the indication of the medical imaging device, a database of device identifications and corresponding operating parameters.

(M7) The method of any one of paragraphs (M1)-(M6), wherein receiving the metadata corresponding to the one or more images captured by the medical imaging device comprises: determining one or more of: a quantity of the one or more images captured by the medical imaging device; whether a pulse setting was activated during capture of the one or more images; or whether an auto setting was activated during capture of the one or more images.

(M8) The method of any one of paragraphs (M1)-(M7), wherein the data is configured to cause the medical imaging device to set an auto feature off and capture a quantity of images at a predetermined frequency.

(M9) The method of any one of paragraphs (M1)-(M8), wherein receiving the patient data comprises receiving the patient data via a user interface of a user device, wherein the patient data indicates a weight of a patient and a height of the patient, and wherein transmitting the data that causes modification of the operating parameters of the medical imaging device comprises: determining an equalizing quotient (EQ), wherein the EQ is calculated by multiplying X by the weight of the patient, wherein X is between 1-10, preferably less than 4, and most preferably between 1-3 to obtain a product, and then dividing the product by the height of the patient; and determining the data by modifying the one or more recommended operating parameter settings based on the EQ. Alternatively, the EQ may be based on a patient's BMI or using a patient silhouette, as described above.

(M10) The method of any one of paragraphs (M1)-(M9), wherein the data is configured to cause the medical imaging device to disable an automatic exposure control setting.

(M11) A method comprising: receiving, by a computing device and from a user device, subject data that comprises a weight of a subject and a height of the subject; automatically determining, by the computing device, operating parameters, for an imaging device, configured to reduce radiation exposure based on: a specific type of imaging procedure to be performed, a target location of the subject, and the subject data, wherein determining the operating parameters comprises determining an Equalizing Quotient (EQ), wherein the EQ is calculated by multiplying X by the weight of the patient, wherein X is between 1-10, preferably less than 4, and most preferably between 1-3 to obtain a product, and then dividing the product by the height of the patient, and wherein the operating parameters comprise one or more of: peak kilovoltage, tube current, or exposure time; and transmitting, by the computing device, the operating parameters to the imaging device; and cause the imaging device to generate an image of the subject using the operating parameters by deactivating an automatic exposure control setting of the imaging device prior to generating the image. Alternatively, the EQ may be based on the patient's BMI or a patient silhouette.

(M12) The method of paragraph (M11), wherein determining the operating parameters further comprises applying the EQ to previously-determined operating parameters.

(M13) The method of any one of paragraphs (M11)-(M12), wherein the imaging device is one or more of: an x-ray device, or a fluoroscopy device.

(M14) The method of any one of paragraphs (M11)-(M13), wherein receiving the subject data comprises: causing the user device to display a user interface; and receiving, via the user interface, input data indicating the weight of a subject and the height of the subject.

(M15) A method for optimizing imaging processes to reduce inadvertent exposure to harmful radiation, the method comprising: causing a user device to display a first user interface; receiving, via the first user interface, an indication of an imaging device; determining, based on the indication of the imaging device, available operating parameters of the imaging device; causing the user interface to display a second user interface; receiving, via the second user interface, subject data comprising: a subject height, a subject weight, body composition data, and a target location of the subject; determining, based on the subject data and the available operating parameters of the imaging device, one or more recommended operating parameter settings by: determining an Equalizing Quotient (EQ), wherein the EQ is calculated by multiplying X by the weight of the patient, wherein X is between 1-10, preferably less than 4, and most preferably between 1-3 to obtain a product, and then dividing the product by the height of the patient; and calculating the one or more recommended operating parameter settings based on the EQ, the body composition data, the target location of the subject, and the available operating parameters of the imaging device; transmitting, to the imaging device, data that causes modification of operating parameters of the imaging device based on the one or more recommended operating parameter settings by causing the imaging device to deactivate an automatic exposure control setting prior to generating the image; and causing the imaging device to capture generate an image of the subject using the operating parameters.

(M16) The method of paragraph (M15), wherein the one or more recommended operating parameter settings comprise one or more of: peak kilovoltage, tube current, or exposure time.

The following paragraphs (A1) through (A16) describe examples of devices that may be implemented based on the present disclosure. These examples may also be implemented in the form of systems, such as systems of multiple devices (e.g., computing devices and imaging devices).

(A1) A computing device configured to use machine learning techniques to optimize medical imaging processes to reduce inadvertent exposure to harmful radiation, the computing device comprising: one or more processors; and memory storing instructions that, when executed by the one or more processors, cause the computing device to: generate a trained machine learning model by training, using training data comprising a history of medical imaging device operating parameter settings, patient data, and imaging results, a machine learning model to output recommended medical imaging device operating parameter settings, wherein training the machine learning model comprises modifying, based on the training data, one or more weights of one or more nodes of an artificial neural network; receive an indication of a medical imaging device; determine, based on the indication of the medical imaging device, available operating parameters of the medical imaging device; receive patient data; provide, to one or more input nodes of the trained machine learning model, the patient data and data corresponding to the available operating parameters of the medical imaging device; receive, via one or more output nodes of the trained machine learning model, one or more recommended operating parameter settings; transmit, to the medical imaging device, data that causes modification of operating parameters of the medical imaging device based on the one or more recommended operating parameter settings; receive metadata corresponding to one or more images captured by the medical imaging device; and further train, based on the metadata, the trained machine learning model.

(A2) The computing device of paragraph (A1), wherein the instructions, when executed by the one or more processors, further cause the computing device to: determine one or more further modifications made to the operating parameters of the medical imaging device, wherein the instructions, when executed by the one or more processors, cause the computing device to further train the trained machine learning model based on the one or more further modifications.

(A3) The computing device of any one of paragraphs (A1)-(A2), wherein the instructions, when executed by the one or more processors, cause the computing device to receive the metadata corresponding to one or more images captured by the medical imaging device by causing the computing device to: determine the metadata by processing the one or more images to identify an image quality for each of the one or more images.

(A4) The computing device of any one of paragraphs (A1)-(A3), wherein the instructions, when executed by the one or more processors, cause the computing device to transmit the data that causes modification of the operating parameters of the medical imaging device by causing the computing device to: determine the data based on: the patient data; and the one or more recommended operating parameter settings.

(A5) The computing device of any one of paragraphs (A1)-(A4), wherein the instructions, when executed by the one or more processors, cause the computing device to receive the patient data by causing the computing device to: cause display, via a user device, of a user interface; and receive, via the user interface, a patient weight and a patient height.

(A6) The computing device of any one of paragraphs (A1)-(A5), wherein the instructions, when executed by the one or more processors, cause the computing device to determine the available operating parameters of the medical imaging device by causing the computing device to: query, based on the indication of the medical imaging device, a database of device identifications and corresponding operating parameters.

(A7) The computing device of any one of paragraphs (A1)-(A6), wherein the instructions, when executed by the one or more processors, cause the computing device to receive the metadata corresponding to the one or more images captured by the medical imaging device by causing the computing device to: determine one or more of: a quantity of the one or more images captured by the medical imaging device; whether a pulse setting was activated during capture of the one or more images; or whether an auto setting was activated during capture of the one or more images.

(A8) The computing device of any one of paragraphs (A1)-(A7), wherein the data is configured to cause the medical imaging device to set an auto feature off and capture a quantity of images at a predetermined frequency.

(A9) The computing device of any one of paragraphs (A1)-(A8), wherein the instructions, when executed by the one or more processors, cause the computing device to receive the patient data by causing the computing device to receive the patient data via a user interface of a user device, wherein the patient data indicates a weight of a patient and a height of the patient, and wherein the instructions, when executed by the one or more processors, cause the computing device to transmit the data that causes modification of the operating parameters of the medical imaging device by causing the computing device to: determine an equalizing quotient (EQ), wherein the EQ is calculated by multiplying X by the weight of the patient, wherein X is between 1-10, preferably less than 4, and most preferably between 1-3 to obtain a product, and then dividing the product by the height of the patient; and determine the data by modifying the one or more recommended operating parameter settings based on the EQ. Alternatively, the EQ may be based on the patient's BMI.

(A10) The computing device of any one of paragraphs (A1)-(A9), wherein the data is configured to cause the medical imaging device to disable an automatic exposure control setting.

(A11) A system comprising: a computing device and an imaging device, wherein the computing device is configured to: receive, from a user device, subject data that comprises a weight of a subject and a height of the subject; automatically determine operating parameters configured to reduce radiation exposure based on: a specific type of imaging procedure to be performed, a target location of the subject, and the subject data, wherein determining the operating parameters comprises determining an Equalizing Quotient (EQ), wherein the EQ is calculated by multiplying X by the weight of the patient, wherein X is between 1-10, preferably less than 4, and most preferably between 1-3 to obtain a product, and then dividing the product by the height of the patient; and wherein the operating parameters comprise one or more of: peak kilovoltage, tube current, or exposure time; and transmit the operating parameters to the imaging device; wherein the imaging device is configured to: in response to receiving the operating parameters from the computing device, generate an image of the subject using the operating parameters by deactivating an automatic exposure control setting of the imaging device prior to generating the image.

(A12) The system of paragraph (A11), wherein determining the operating parameters further comprises applying the EQ to determine the operating parameters.

(A13) The system of any one of paragraphs (A11)-(A12), wherein the imaging device is one or more of: an x-ray device, or a fluoroscopy device.

(A14) The system of any one of paragraphs (A11)-(A13), wherein the computing device is configured to receive the subject data by: causing the user device to display a user interface; and receiving, via the user interface, input data indicating the weight of a subject and the height of the subject.

(A15) A computing device comprising one or more processors and memory storing instructions that, when executed by the one or more processors, cause the computing device to: cause a user device to display a first user interface; receive, via the first user interface, an indication of an imaging device; determine, based on the indication of the imaging device, available operating parameters of the imaging device; cause the user interface to display a second user interface; receive, via the second user interface, subject data comprising: a subject height, a subject weight, body composition data, and a target location of the subject; determine, based on the subject data and the available operating parameters of the imaging device, one or more recommended operating parameter settings by: determining an Equalizing Quotient (EQ), wherein the EQ is calculated by multiplying X by the weight of the patient, wherein X is between 1-10, preferably less than 4, and most preferably between 1-3 to obtain a product, and then dividing the product by the height of the patient; and calculating the one or more recommended operating parameter settings based on the EQ, the body composition data, the target location of the subject, and the available operating parameters of the imaging device; transmit, to the imaging device, data that causes modification of operating parameters of the imaging device based on the one or more recommended operating parameter settings by causing the imaging device to deactivate an automatic exposure control setting prior to generating the image; and cause the imaging device to capture generate an image of the subject using the operating parameters.

(A16) The computing device of paragraph (A15), wherein the one or more recommended operating parameter settings comprise one or more of: peak kilovoltage, tube current, or exposure time.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
a computing device and an imaging device,
wherein the computing device is configured to:
  receive, from a user device, subject data that comprises a weight of a subject and a height of the subject;
  automatically determine operating parameters configured to reduce radiation exposure based on:
    a specific type of imaging procedure to be performed,
    a target location of the subject, and
    the subject data, wherein determining the operating parameters comprises determining an Equalizing Quotient (EQ), wherein the EQ is calculated by multiplying X by the weight of the subject, wherein X is between 1-10, preferably less than 4, and most preferably between 1-3 to obtain a product, and then dividing the product by the height of the subject, and wherein the operating parameters comprise one or more of:
      peak kilovoltage,
      tube current, or
      exposure time; and
  transmit the operating parameters to the imaging device;
wherein the imaging device is configured to:
  in response to receiving the operating parameters from the computing device, generate an image of the subject using the operating parameters.

2. The system of claim 1, further comprising using the EQ to define the operating parameters.

3. The system of claim 1, wherein the imaging device is one or more of:
an x-ray device, or
a fluoroscopy device.

4. The system of claim 1, wherein the computing device is configured to receive the subject data by:
causing the user device to display a user interface; and
receiving, via the user interface, input data indicating the weight of a subject and the height of the subject.

5. The system of claim 1, wherein the computing device is configured to deactivate an automatic exposure control setting of the imaging device prior to generating the image.

6. A method comprising:
receiving, by a computing device and from a user device, subject data that comprises a weight of a subject and a height of the subject;
automatically determining, by the computing device, operating parameters, for an imaging device, configured to reduce radiation exposure based on:
  a specific type of imaging procedure to be performed,
  a target location of the subject, and
  the subject data, wherein determining the operating parameters comprises determining an Equalizing Quotient (EQ), wherein the EQ is calculated by multiplying X by the weight of the subject, wherein X is between 1-10, preferably less than 4, and most preferably between 1-3 to obtain a product, and then dividing the product by the height of the subject, and wherein the operating parameters comprise one or more of:
    peak kilovoltage,
    tube current, or
    exposure time; and
transmitting, by the computing device, the operating parameters to the imaging device; and
cause the imaging device to generate an image of the subject using the operating parameters by deactivating an automatic exposure control setting of the imaging device prior to generating the image.

7. The method of claim 6, wherein determining the operating parameters further comprises using the EQ to define the operating parameters.

8. The method of claim 6, wherein the imaging device is one or more of:
an x-ray device, or
a fluoroscopy device.

9. The method of claim 6, wherein receiving the subject data comprises:
causing the user device to display a user interface; and
receiving, via the user interface, input data indicating the weight of a subject and the height of the subject.

10. A method for optimizing imaging processes to reduce inadvertent exposure to harmful radiation, the method comprising:
causing a user device to display a first user interface;
receiving, via the first user interface, an indication of an imaging device;
determining, based on the indication of the imaging device, available operating parameters of the imaging device;
causing the user interface to display a second user interface;
receiving, via the second user interface, subject data comprising:
  a subject height,
  a subject weight,
  body composition data, and
  a target location of the subject;
determining, based on the subject data and the available operating parameters of the imaging device, one or more recommended operating parameter settings by:
  determining an Equalizing Quotient (EQ), wherein the EQ is calculated by multiplying X by the weight of the subject, wherein X is between 1-10, preferably less than 4, and most preferably between 1-3 to obtain a product, and then dividing the product by the height of the subject; and
  calculating the one or more recommended operating parameter settings based on the EQ, the body composition data, the target location of the subject, and the available operating parameters of the imaging device;
transmitting, to the imaging device, data that causes modification of operating parameters of the imaging device based on the one or more recommended operating parameter settings; and
causing the imaging device to capture generate an image of the subject using the operating parameters.

11. The method of claim 10, wherein the one or more recommended operating parameter settings comprise one or more of:
peak kilovoltage,
tube current, or
exposure time.

12. A system comprising:
a computing device and an imaging device,
wherein the computing device is configured to:
  receive, from a user device, subject data that comprises a weight of a subject and a height of the subject;
  automatically determine operating parameters configured to reduce radiation exposure based on:
    a specific type of imaging procedure to be performed,
    a target location of the subject, and
    the subject data, wherein determining the operating parameters comprises determining an Equalizing Quotient (EQ), wherein the EQ is calculated by multiplying X by the weight of the subject, wherein X is between 1-10, and then dividing the product by the height of the subject, and wherein the operating parameters comprise one or more of:
      peak kilovoltage,
      tube current, or
      exposure time; and
  transmit the operating parameters to the imaging device;
wherein the imaging device is configured to:
  in response to receiving the operating parameters from the computing device, generate an image of the subject using the operating parameters.

13. The system of claim 12, wherein X is less than 4.

14. The system of claim 13, wherein X is between 1-3.

* * * * *